United States Patent
Abribat

(10) Patent No.: US 9,920,311 B2
(45) Date of Patent: Mar. 20, 2018

(54) PEGYLATED L-ASPARAGINASE

(71) Applicant: ALIZE PHARMA II SAS, Ecully (FR)

(72) Inventor: Thierry Abribat, Sainte Foy les Lyon (FR)

(73) Assignee: Jazz Pharmaceuticals II SAS, Lyons (FR)

( * ) Notice: Subject to any disclaimer, the term of this patent is extended or adjusted under 35 U.S.C. 154(b) by 0 days.

(21) Appl. No.: 14/819,305

(22) Filed: Aug. 5, 2015

(65) Prior Publication Data

US 2016/0060613 A1    Mar. 3, 2016

Related U.S. Application Data

(63) Continuation of application No. 13/382,276, filed as application No. PCT/EP2010/059599 on Jul. 6, 2010, now abandoned.

(60) Provisional application No. 61/223,320, filed on Jul. 6, 2009.

(30) Foreign Application Priority Data

Mar. 30, 2010    (WO) ................ PCT/EP2010/054156

(51) Int. Cl.
 A61K 38/00    (2006.01)
 C12N 9/82    (2006.01)
 A61K 38/50    (2006.01)
 C12N 9/96    (2006.01)
 A61K 47/60    (2017.01)

(52) U.S. Cl.
 CPC ............... *C12N 9/82* (2013.01); *A61K 38/50* (2013.01); *A61K 47/60* (2017.08); *C12N 9/96* (2013.01); *C12Y 305/01001* (2013.01)

(58) Field of Classification Search
 None
 See application file for complete search history.

(56) References Cited

U.S. PATENT DOCUMENTS

| | | |
|---|---|---|
| 5,286,637 A | 2/1994 | Veronese et al. |
| 5,359,030 A | 10/1994 | Ekwuribe et al. |
| 5,681,811 A | 10/1997 | Ekwuribe et al. |
| 5,932,462 A | 8/1999 | Harris et al. |
| 6,309,633 B1 | 10/2001 | Ekwuribe et al. |
| 7,419,660 B1 | 9/2008 | Harris et al. |
| 7,786,221 B2 | 8/2010 | Harris et al. |
| 7,829,320 B2 | 11/2010 | Matsui et al. |
| 7,871,806 B2 | 1/2011 | Matsui et al. |
| 8,354,477 B2 | 1/2013 | Harris et al. |

FOREIGN PATENT DOCUMENTS

WO    WO 03/018742 A2    3/2003

OTHER PUBLICATIONS

Billett et al., Allergic reactions to Erwinia asparaginase in children with acute lymphoblastic leukemia who had previous allergic reactions to Escherichia coli asparaginase, Cancer, 1992, vol. 70, pp. 201-206.
Albertsen et al., Comparison of intramuscular therapy with Erwinia asparaginase and asparaginase Medac: Pharmacokinetics, pharmacodynamics, formation of antibodies and influence on the coagulation system, British Journal of Haematology, 2001, vol. 115, pp. 983-990.
Duval et al., Comparison of *Escherichia coli*-asparaginase with Erwinia-asparaginase in the treatment of childhood lymphoid malignancies: results of a randomized European Organization for Research and Treatment of Cancer-Children's Leukemia Group phase 3 trial, Blood, 2002, vol. 99, pp. 2734-2739.
Roberts et al., Chemistry for peptide and protein PEGylation, Advanced Drug Delivery Reviews, 2002, vol. 54, pp. 459-476.
Graham, Pegaspargase: a review of clinical studies, Advanced Drug Delivery Reviews, 2003, vol. 55, No. 10, pp. 1293-1302.
Sokolov et al,, Design of recombinant L-Asparaginase erwinia carotovora drug with an antitumor action, Molekuiyarnaya Meditsina, Izdatel'stvo Meditsina, Ru, 2005, vol. 1, pp. 45-53 (See English Abstract).
Avramis et al., Pharrnacokinetic/pharrnacodynarnic relationships of asparaginase formulations: the past, the present and recommendations for the future, Clinical Pharmacokinetics, 2005, vol. 44, pp. 367-393.
Kuchumova et al., Modification of recombinant asparaginase from Erwinia carotovora with polyethylene glycol 5000, Biochemistry (Moscow) supplemental series B: Biomedical Chemistry, 2007, vol. 1, pp. 230-232.
Sartore et al,, Accurate Evaluation Method of the Polymer Content in Monomethoxy (Polyethylene Glycol) Modified Proteins Based on Amino Acid Analysis, Applied Biochemistry and Biotechnology, 1991, 31: 213-222.
Veronese et al., Improvement of pharmacokinetic, immunological and stability properties of asparaginase by conjugation to linear and branched rnonomethoxy poly( ethylene glycol), Journal of Controlled Release, 1996, 40: 199-209.
Oncaspar (pegaspargase) injection for intramuscular or intravenous use, product insert, pp. 1-2, Feb. 1, 1994; Sigma-Tau Pharmaceuticals, Inc., Gaithersburg, Maryland, USA.

(Continued)

*Primary Examiner* — Hope Robinson
(74) *Attorney, Agent, or Firm* — Morgan, Lewis & Bockius LLP

(57) ABSTRACT

Disclosed is a conjugate of a protein having substantial L-asparagine aminohydrolase activity and polyethylene glycol. In particular, the polyethylene glycol has a molecular weight less than or equal to about 5000 Da and the protein is an L-asparaginase from *Erwinia*. The conjugate of the invention has shown superior properties such as maintenance of a high level of in vitro activity and an unexpected increase in half-life in vivo. Also disclosed are methods of producing the conjugate and use of the conjugate in therapy. In particular, a method is disclosed for use of the conjugate in the treatment of cancer, particularly Acute Lymphoblastic Leukemia (ALL). More specifically, a method is disclosed for use of the conjugate as a second line therapy for patients who have developed hypersensitivity or have had a disease relapse after treatment with other L-asparaginase preparations.

14 Claims, 15 Drawing Sheets

(56) References Cited

OTHER PUBLICATIONS

Figure 1:
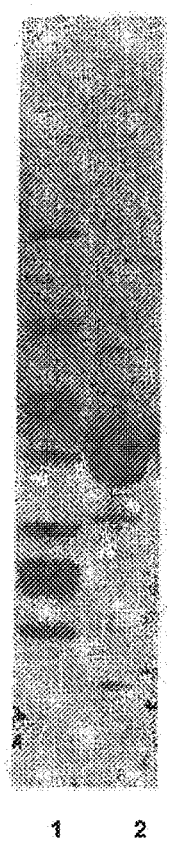

Minton et al., Nucleotide sequence of the Erwinia chrysanthemi NCPPB 1066 L-asparaginase gene, Gene, vol. 46, pp. 25-35, 1986.
Miller et al., A left-handed crossover involved in amidohydrolase catalysis Crystal structure of Erwinia chrysanthemi L-asparaginase with bound L-aspartateFEBS Lett., 1993, vol. 328, No. 3, pp. 275-279.
Keating et al., L-Asparaginase and PEG Asparaginase—Past, Present, and Future, Leukemia and Lymphoma, vol. 10, pp. 153-157, 1993
Abshire et al,, Weekly polyethylene glycol conjugated L-asparaginase compared with biweekly dosing produces superior induction remission rates in childhood relapsed acute lymphoblastic leukemia: a pediatric oncology group study, Blood, 2000, vol. 96, pp. 1709-1715.
Fu et al., PEG-Asparaginase, Expert Opin. Pharmacother, 2007, vol. 8, No. 12, pp. 1977-1984.
Genbank sequence: CAA31239, Oct. 23, 2008.
Genbank sequence: AAS67028, Jan. 8, 2007.
Roberts at al. Chemistry for peptide and protein PEGylation, Advanced Drug Delivery Reviews, 2002, vol. 54, pp. 459-476.
Park et al., Pharmacology of *Escherichia coli*-L-Asparaginase Polyethylene Glycol Adduct, Anti-cancer Research, 1981, vol. 1, pp. 373-376.
Chien et al., Pharmacology, immunogenicity, and efficacy of a novel pegylated recombinant Erwinia chrysanthemi-derived L-asparaginase, Invest, New Drug, 2014, vol. 45, pp. 1-16.
Yang, PEGylation—Successful Approach for Therapeutic Protein Conjugation, Mod. Chem, Appl, 2013, vol. 1:4-5.
Chunhua et al., New administration system—conjugate of protein or polypeptide drug and polyethylene glycol, Chinese Pharmacy Journal, vol. 36, pp. 292-296 (2001) (see translated office action in the corresponding Chinese patent application No. 201080030392.6).
Jiahua et al., Effects of the Lys190 in antigenic epitopes of recombinant *E. coli* L-asparaginase on its antigenicity, Journal of China Pharmaceutical University, vol. 37, pp. 277-280 (2006).
Office Action issued in the corresponding Chinese patent application No. 201080030392.6 dated Mar. 25, 2013.
"Erwinia chrysanthemi," Data Sheets on Quarantine Pests, prepared by the Centre for Agriculture and Biosciences International (CABI) and the European and Mediterranean Plant Protection Organization (EPPO) for the European Union, available online at www.eppo.int/QUARANTINE/data_sheets/bacteria/ERWICH_ds.pdf (available at least as early as Mar. 10, 2016).

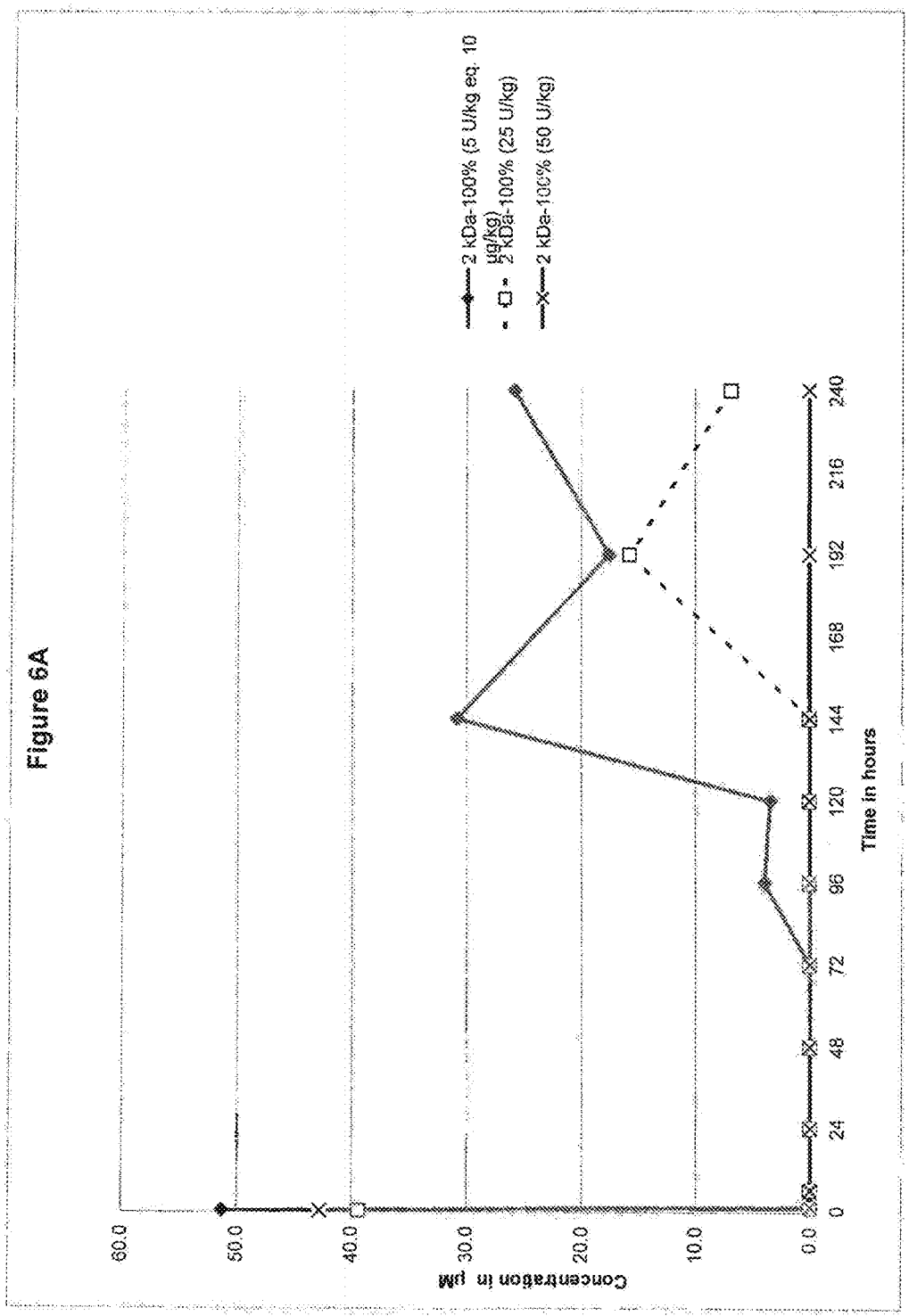

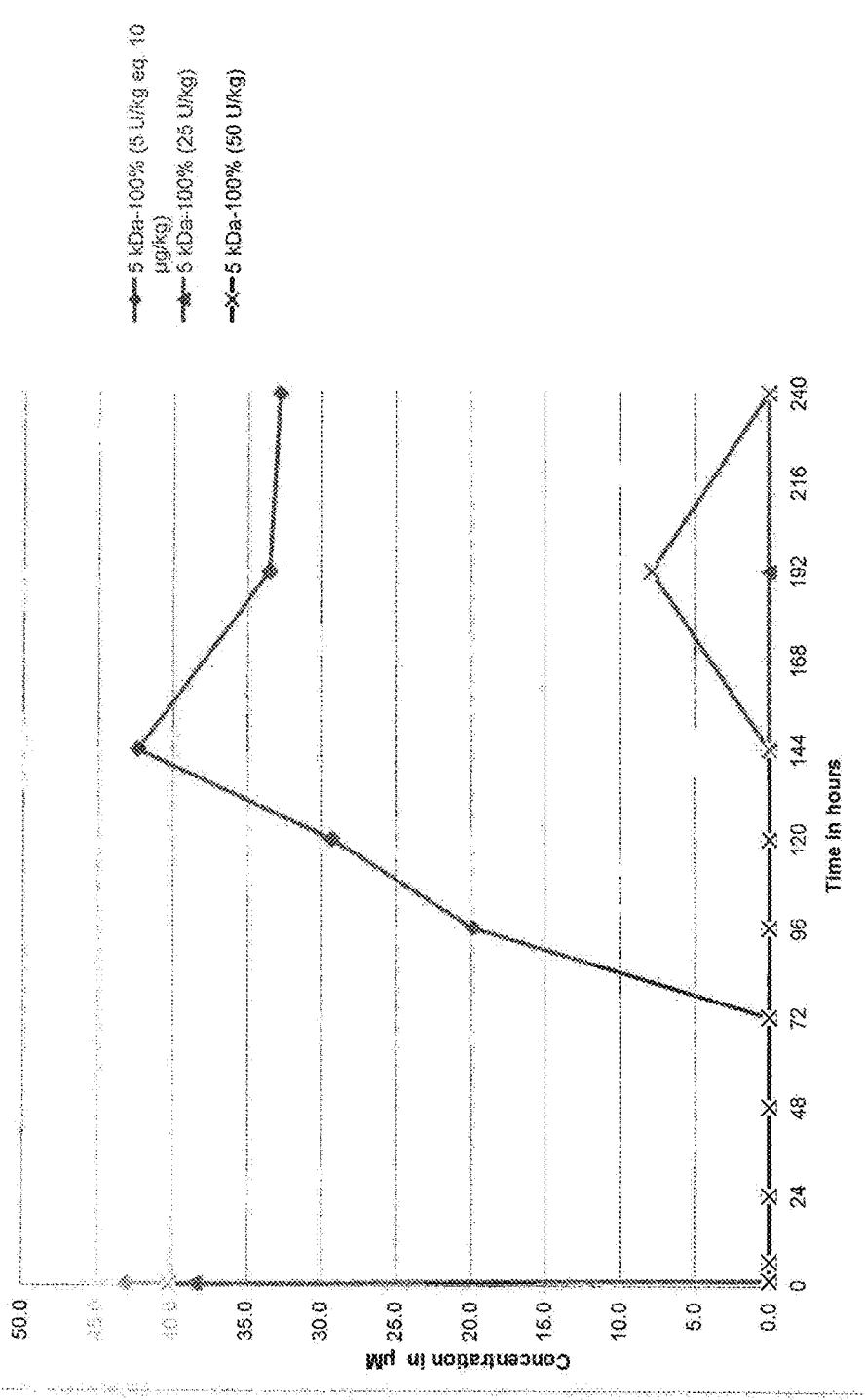

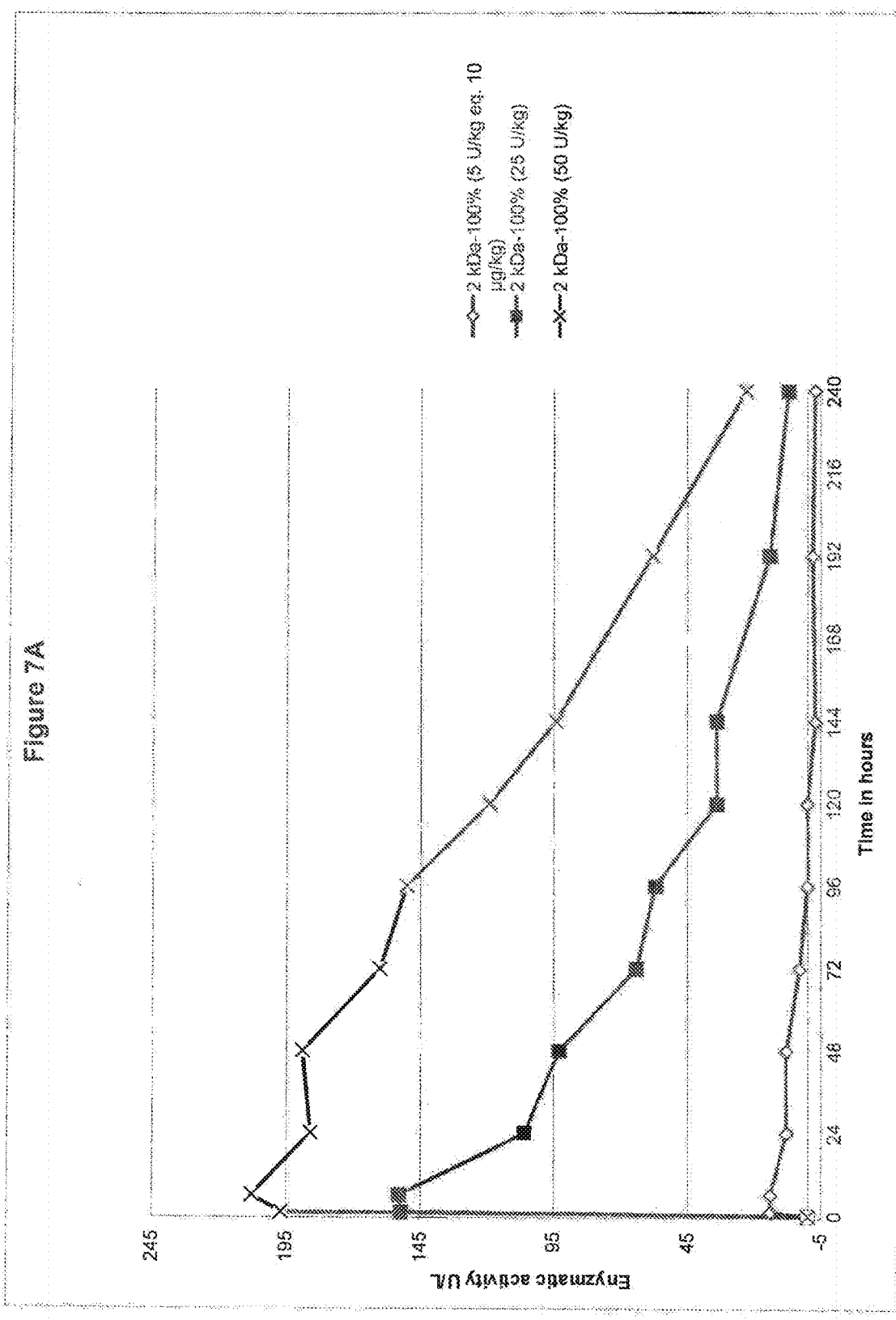

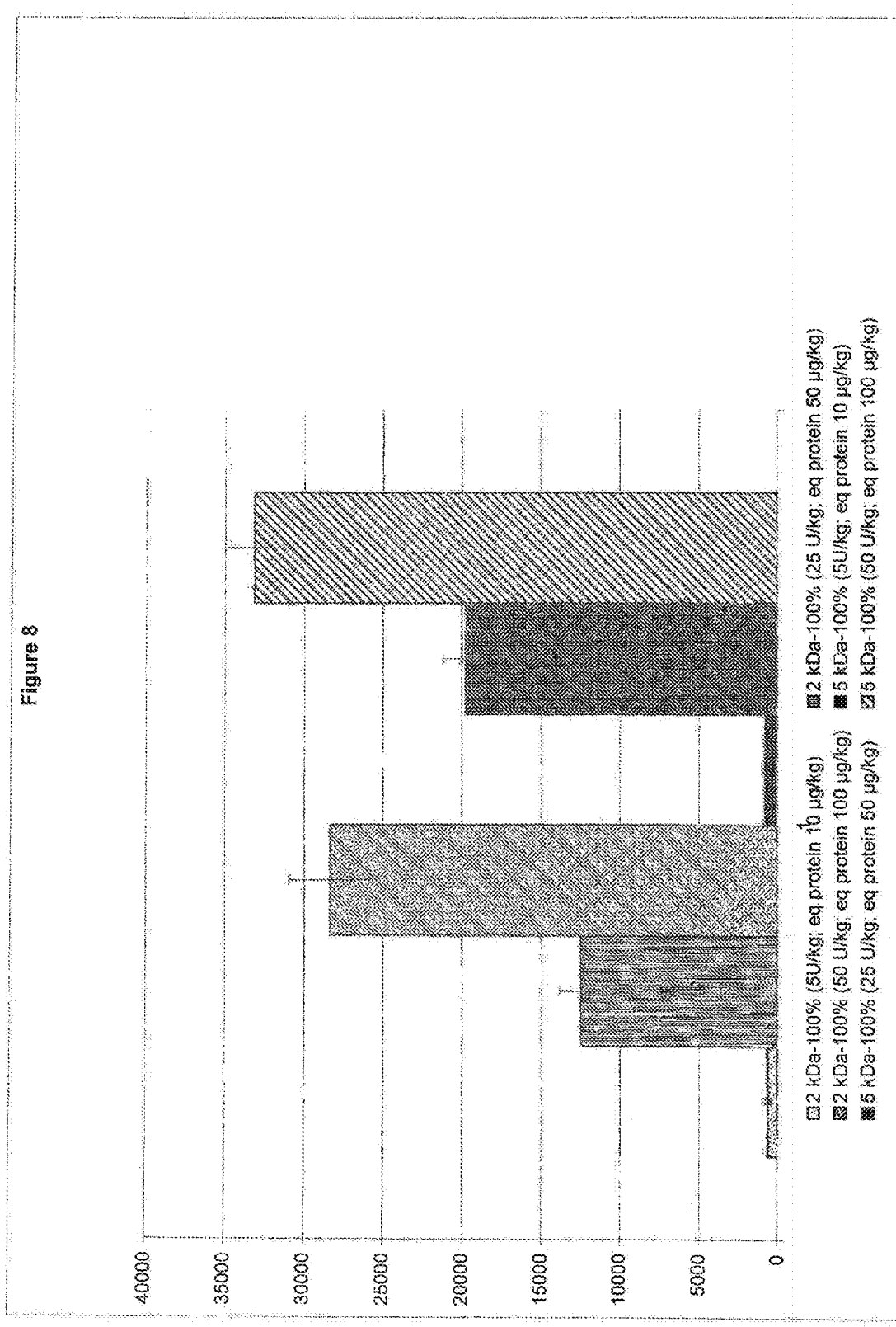

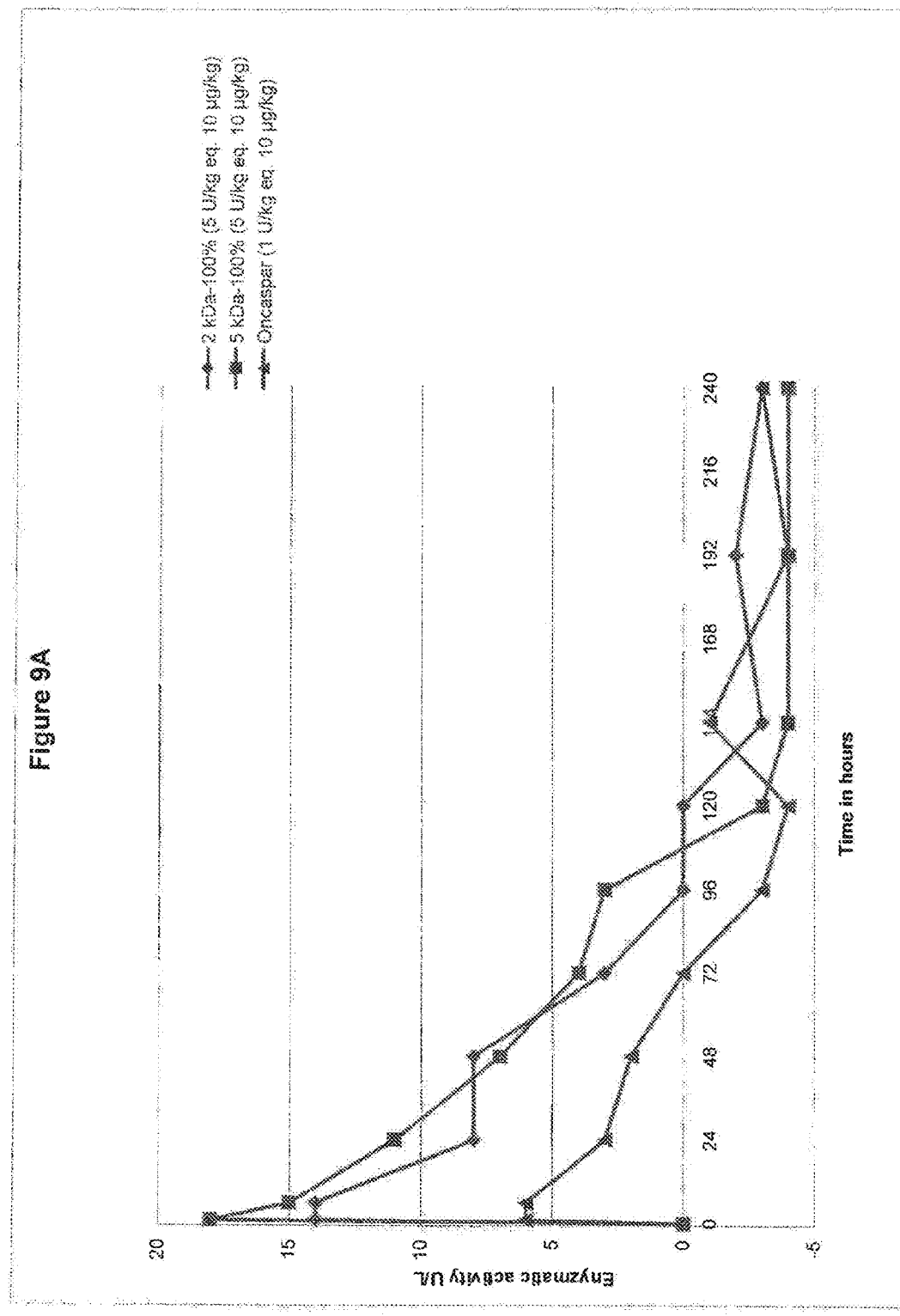

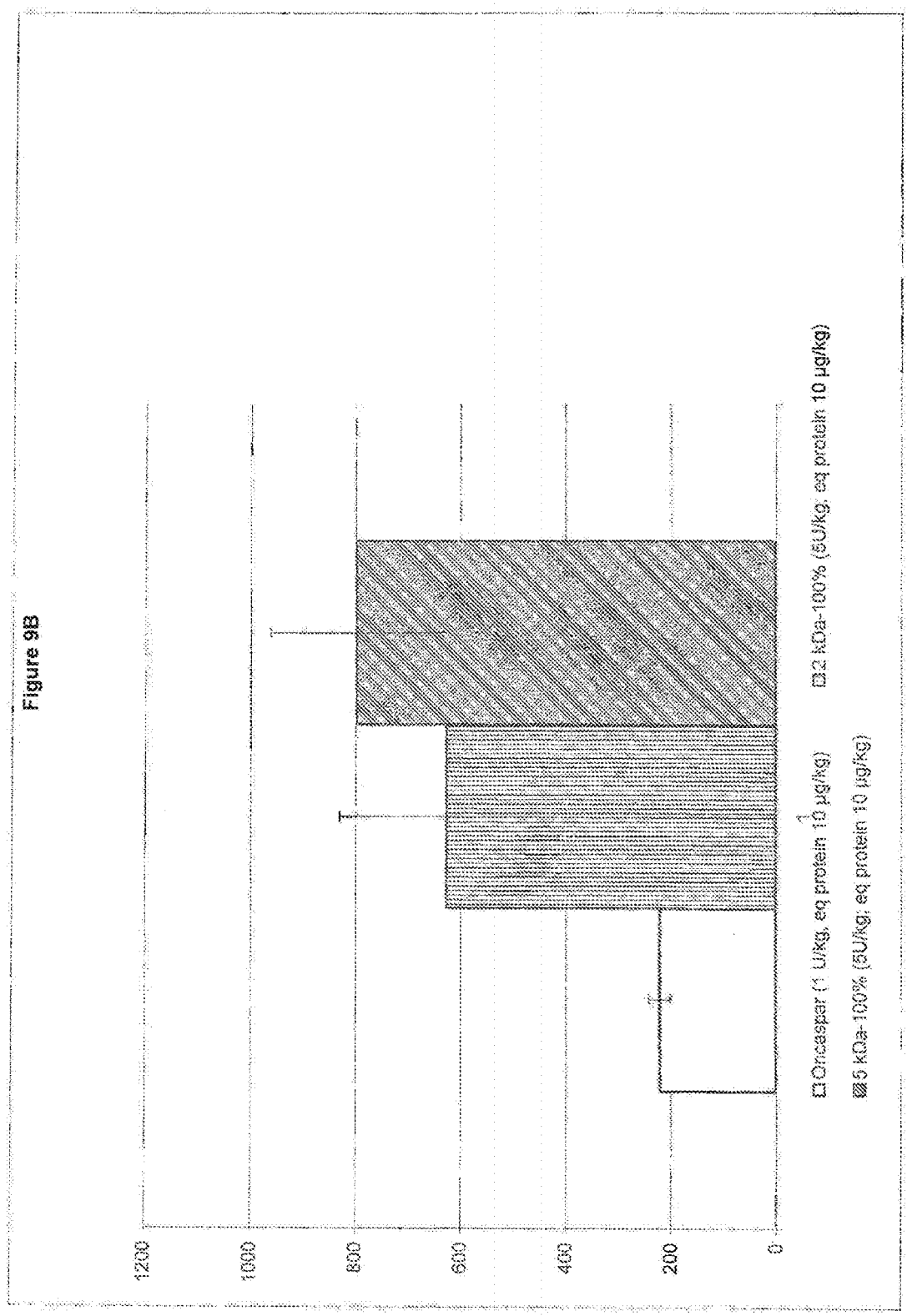

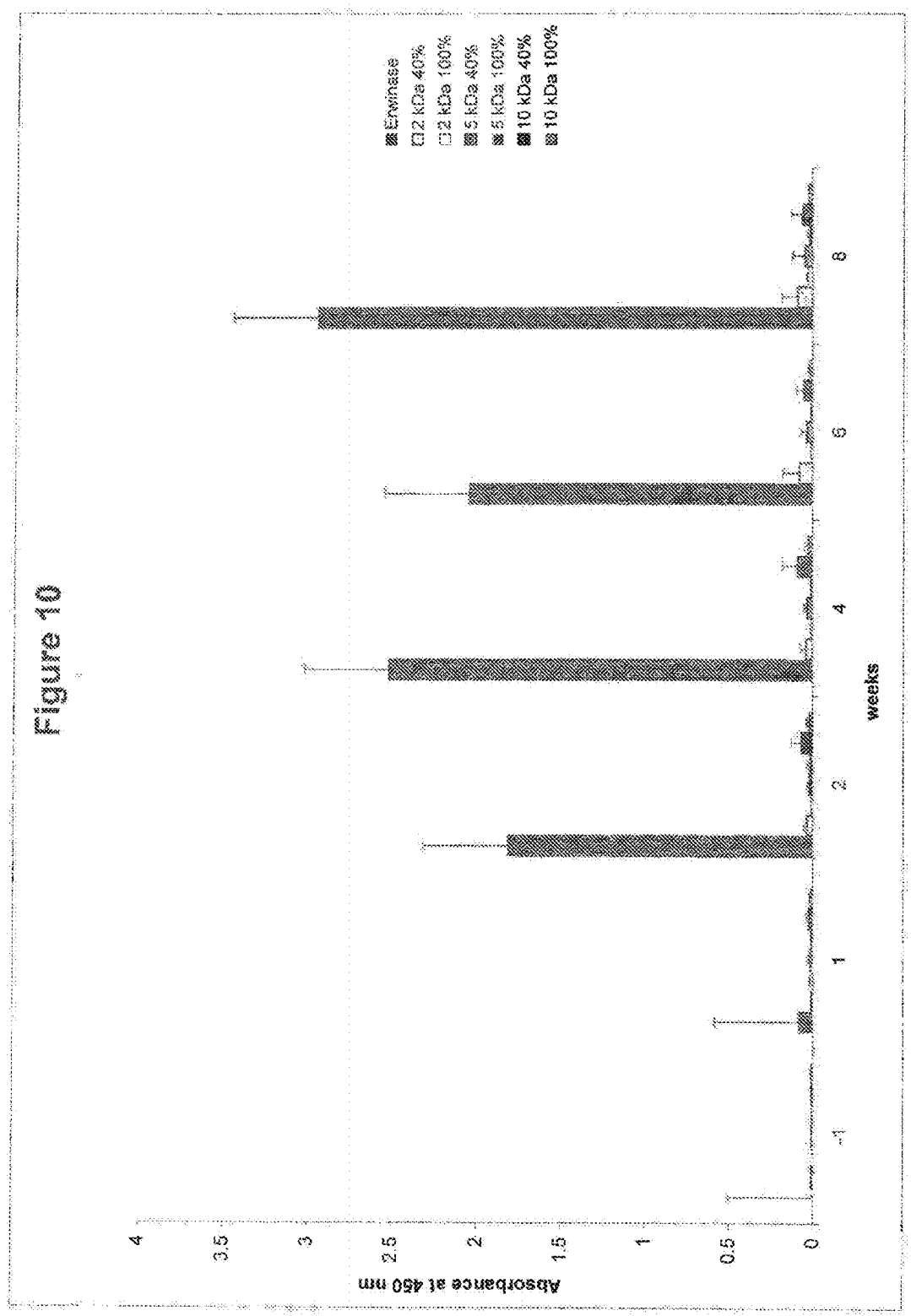

Figure 11
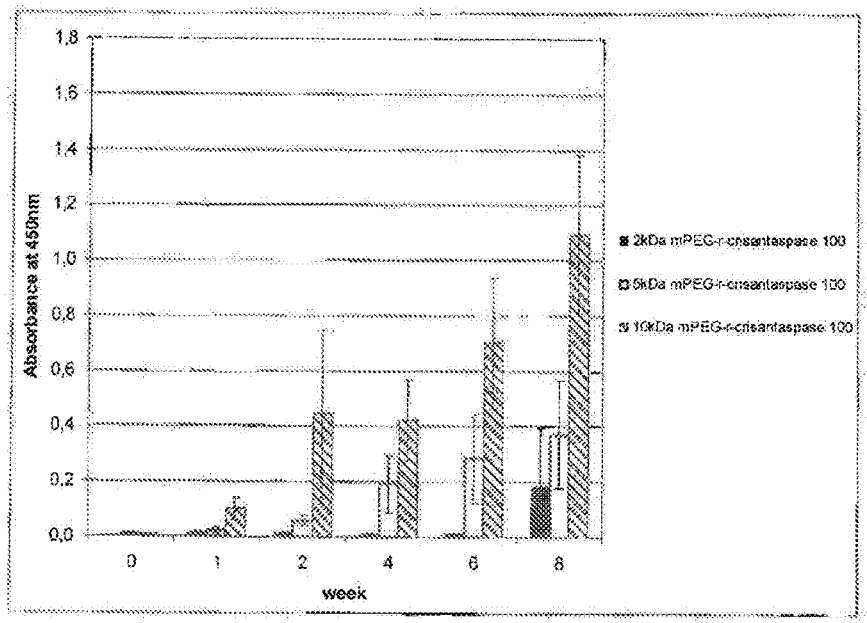
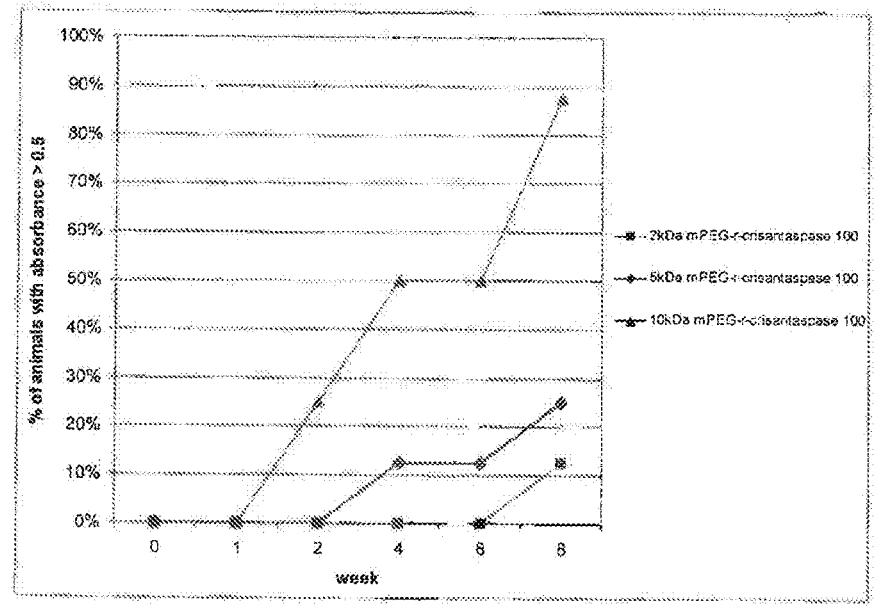

PEGYLATED L-ASPARAGINASE

BACKGROUND OF THE INVENTION

Field of the Invention

The present invention concerns a conjugate of a protein having substantial L-asparagine aminohydrolase activity and polyethylene glycol, particularly wherein the polyethylene glycol has a molecular weight less than or equal to about 5000 Da, particularly a conjugate wherein the protein is a L-asparaginase from *Erwinia*, and its use in therapy.

Background

Proteins with L-asparagine aminohydrolase activity, commonly known as L-asparaginases, have successfully been used for the treatment of Acute Lymphoblastic Leukemia (ALL) in children for many years. ALL is the most common childhood malignancy (Avramis and Panosyan, (2005) 44:367-393).

L-asparaginase has also been used to treat Hodgkin's disease, acute myelocytic Leukemia, acute myclomonocytic Leukemia, chronic lymphocytic Leukemia, lymphosarcoma, reticulosarcoma, and melanosarcoma (Kotzia and Labrou, *J. Biotechnol.* 127 (2007) 657-669). The anti-tumor activity of L-asparaginase is believed to be due to the inability or reduced ability of certain malignant cells to synthesize L-asparagine (Kotzia and Labrou, *J. Biotechnol.* 127 (2007) 657-669). These malignant cells rely on an extracellular supply of L-asparagine. However, the L-asparaginase enzyme catalyzes the hydrolysis of L-asparagine to aspartic acid and ammonia, thereby depleting circulating pools of L-asparagine and killing tumor cells which cannot perform protein synthesis without L-asparagine (Kotzia and Labrou, *J. Biotechnol.* 127 (2007) 657-669).

L-asparaginase from *E. coli* was the first enzyme drug used in ALL therapy and has been marketed as Elspar® in the USA or as Kidrolase® and L-asparaginase Medac® in Europe. L-asparaginases have also been isolated from other microorganisms, e.g., an L-asparaginase protein from *Erwinia chrysanthemi*, named crisantaspase, that has been marketed as Erwinase® (Wriston Jr., J. C. (1985) "L-asparaginase" *Meth. Enzymol.* 113, 608-618; Goward, C. R. et. al (1992) "Rapid large scale preparation of recombinant *Erwinia chrysanthemi* L-asparaginase", Bioseparation 2, 335-341). L-asparaginases from other species of *Erwinia* have also been identified, including, for example, *Erwinia chrysanthemi* 3937 (Genbank Accession #AAS67028), *Erwinia chrysanthemi* NCPPB 1125 (Genbank Accession #CAA31239), *Erwinia carotovora* (Genbank Accession #AAP92666), and *Erwinia carotovora* subsp. Astroseptica (Genbank Accession #AAS67027). These *Erwinia chrysanthemi* L-asparaginases have about 91-98% amino acid sequence identity with each other, while the *Erwinia carotovora* L-asparaginases have approximately 75-77% amino acid sequence identity with the *Erwinia chrysanthemi* L-asparaginases (Kotzia and Labrou, *J. Biotechnol.* 127 (2007) 657-669).

L-asparaginases of bacterial origin have a high immunogenic and antigenic potential and frequently provoke adverse reactions ranging from mild allergic reaction to anaphylactic shock in sensitized patients (Wang, B. et. al (2003) "Evaluation of immunologic cross reaction of anti-asparaginase antibodies in acute lymphoblastic Leukemia (ALL and lymphoma patients), *Leukemia* 17, 1583-1588). *E. coli* L-asparaginase is particularly immunogenic, with reports of the presence of anti-asparaginase antibodies to *E. coli* L-asparaginase following i.v. or i.m. administration reaching as high as 78% in adults and 70% in children (Wang, B. et. al (2003) *Leukemia* 17, 1583-1588).

L-asparaginases from *Escherichia Coli* and *Erwinia chrysanthemi* differ in their pharmacokinetic properties and have distinct immunogenic profiles, respectively (Klug Albertsen, B. et. al (2001) "Comparison of intramuscular therapy with *Erwinia* asparaginase and asparaginase Medac: pharmacokinetics. pharmacodynamics, formation of antibodies and influence on the coagulation system" Brit. J. Haematol. 115, 983-990). Furthermore, it has been shown that antibodies that developed after a treatment with L-asparaginase from *E. coli* do not cross react with L-Asparaginase from *Erwinia* (Wang, B. et. al, *Leukemia* 17 (2003) 1583-1588). Thus, L-asparaginase from *Erwinia* (crisantaspase) has been used as a second line treatment of ALL in patients that react to *E. coli* L-asparaginase (Duval, M. et. al (2002) "Comparison of *Escherichia Coli*-asparaginase with *Erwinia*-asparaginase in the treatment of childhood lymphoid malignancies: results of a randomized European Organisation for Research and Treatment of Cancer, Children's Leukemia Group phase 3 trial" Blood 15, 2734-2739; Avramis and Panosyan, Clin. Pharmacokinet. (2005) 44:367-393).

In another attempt to reduce immunogenicity associated with administration of microbial L-asparaginases, an *E. coli* L-asparaginase has been developed that is modified with methoxy-polyethyleneglycol (mPEG). This method is commonly known as "PEGylation" and has been shown to alter the immunological properties of proteins (Abuchowski, A. et. al (1977) "Alteration of Immunological Properties of Bovine Serum Albumin by Covalent Attachment of Polyethylene Glycol," *J. Biol. Cheni.* 252 (11), 3578-3581). This so-called mPEG-L-asparaginase, or pegaspargase, marketed as Oncaspar® (Enzon Inc., USA), was first approved in the U.S. for second line treatment of ALL in 1994, and has been approved for first-line therapy of ALL in children and adults since 2006. Oncaspar® has a prolonged in vivo half-life and a reduced immunogenicity/antigenicity.

Oncaspar® is *E. coli* L-asparaginase that has been modified at multiple lysine residues using 5 kDa mPEG-succinimidyl succinate (SS-PEG) (U.S. Pat. No. 4,179,337). SS-PEG is a PEG reagent of the first generation that contains an instable ester linkage that is sensitive to hydrolysis by enzymes or at slightly alkaline pH values (U.S. Pat. No. 4,670,417; *Makromol. Chem.* 1986, 187, 1131-1144). These properties decrease both in vitro and in vivo stability and can impair drug safety.

Furthermore, it has been demonstrated that antibodies developed against L-asparaginase from *E. coli* will cross react with Oncaspar® (Wang, B. et. al (2003) "Evaluation of immunologic cross-reaction of anti-asparaginase antibodies in acute lymphoblastic Leukemia (ALL and lymphoma patients)," *Leukemia* 17, 1583-1588). Even though these antibodies were not neutralizing, this finding clearly demonstrated the high potential for cross-hypersensitivity or cross-inactivation in vivo. Indeed, in one report 30-41% of children who received pegaspargase had an allergic reaction (Wang, B. et. al (2003) *Leukemia* 17, 1583-1588).

In addition to outward allergic reactions, the problem of "silent hypersensitivity" was recently reported, whereby patients develop anti-asparaginase antibodies without showing any clinical evidence of a hypersensitivity reaction (Wang, B. et. al (2003) *Leukemia* 17, 1583-1588). This reaction can result in the formation of neutralizing antibodies to *E. coli* L-asparaginase and pegaspargase; however, these patients are not switched to *Erwinia* L-asparaginase because there are not outward signs of hypersensitivity, and therefore they receive a shorter duration of effective treatment (Holcenberg, J., *J. Pediatr. Hematol. Oncol.* 26 (2004) 273-274).

*Erwinia chrysanthemi* L-asparaginase treatment is often used in the event of hypersensitivity to *E. coli*-derived L-asparaginases. However, it has been observed that as many as 30-50% of patients receiving *Erwinia* L-asparaginase are antibody-positive (Avramis and Panosyan, Clin. Pharmacokinet. (2005) 44:367-393). Moreover, because *Erwinia chrysanthemi* L-asparaginase has a significantly shorter elimination half-life than the *E. coli* L-asparaginases, it must be administered more frequently (Avramis and Panosyan, Clin. Pharmacokinet. (2005) 44:367-393). In a study by Avramis et. al, *Erwinia* asparaginase was associated with inferior pharmacokinetic profiles (Avramis et. al, *J. Pediatr. Hematol. Oncol.* 29 (2007) 239-247). *E. coli* L-asparaginase and pegaspargase therefore have been the preferred first-line therapies for ALL over *Erwinia* L-asparaginase.

Numerous biopharmaceuticals have successfully been PEGylated and marketed for many years. In order to couple PEG to a protein, the PEG has to be activated at its OH terminus. The activation group is chosen based on the available reactive group on the protein that will be PEGylated. In the case of proteins, the most important amino acids are lysine, cysteine, glutamic acid, aspartic acid, C-terminal carboxylic acid and the N-terminal amino group. In view of the wide range of reactive groups in a protein nearly the entire peptide chemistry has been applied to activate the PEG moiety. Examples for this activated PEG-reagents are activated carbonates, e.g., p-nitrophenyl carbonate, succinimidyl carbonate; active esters, e.g., succinimidyl ester; and for site specific coupling aldehydes and maleimides have been developed (Harris, M., Adv. Drug Del. Rev. 54 (2002), 459-476). The availability of various chemical methods for PEG modification shows that each new development of a PEGylated protein will be a case by case study. In addition to the chemistry the molecular weight of the PEG that is attached to the protein has a strong impact on the pharmaceutical properties of the PEGylated protein. In most cases it is expected that, the higher the molecular weight of the PEG, the better the improvement of the pharmaceutical properties (Sherman, M. R., Adv. Drug Del. Rev. 60 (2008), 59-68; Holtsberg, F. W., *Journal of Controlled Release* 80 (2002), 259-271). For example, Holtsberg et al. found that, when PEG was conjugated to arginine deaminase, another amino acid degrading enzyme isolated from a microbial source, pharmacokinetic and pharmacodynamic function of the enzyme increased as the size of the PEG attachment increased from a molecular weight of 5000 Da to 20,000 Da (Holtsberg, F. W., Journal of Controlled Release 80 (2002), 259-271).

However, in many cases, PEGylated biopharmaceuticals show significantly reduced activity compared to the unmodified biopharmaceutical (Fishburn, C. S. (2008) Review "The Pharmacology of PEGylation: Balancing PD with PK to Generate Novel Therapeutics" *J. Pharm. Sci.*, 1-17). In the case of L-asparaginase from *Erwinia carotovora*, it has been observed that PEGylation reduced its in vitro activity to approximately 57% (Kuchumova, A. V. et. al (2007) "Modification of Recombinant asparaginase from *Erwinia carotovora* with Polyethylene Glycol 5000" *Biochemistry* (Moscow) Supplement Series B: Biomedical Chemistry, 1, 230-232). The L-asparaginase from *Erwinia carotovora* has only about 75% homology to the *Erwinia chrysanthemi* L-asparaginase (crisantaspase). For Oncaspar® it is also known that its in vitro activity is approximately 50% compared to the unmodified *E. coli* L-asparaginase.

The currently available L-asparaginase preparations do not provide alternative or complementary therapies—particularly therapies to treat ALL—that are characterized by high catalytic activity and significantly improved pharmacological and pharmacokinetic properties, as well as reduced immunogenicity.

BRIEF SUMMARY OF THE INVENTION

The present invention is directed to a conjugate of a protein having substantial L-asparagine aminohydrolase activity and polyethylene glycol, wherein the polyethylene glycol has a molecular weight less than or equal to about 5000 Da, particularly a conjugate where the protein is a L-asparaginase from *Erwinia*. In one embodiment, the conjugate comprises an L-asparaginase from *Erwinia* having at least 80% identity to the amino acid of SEQ ID NO: 1 and polyethylene glycol (PEG), wherein the PEG has a molecular weight less than or equal to about 5000 Da. In one embodiment, the L-asparaginase has at least about 80%, 85%, 90%, 91%, 92%, 93%, 94%, 95%, 96%, 97%, 98%, 99%, or 100% identity to the amino acid of SEQ ID NO: 1. In some embodiments, the PEG has a molecular weight of about 5000 Da, 4000, Da, 3000 Da, 2500 Da, or 2000 Da. In one embodiment, the conjugate has an in vitro activity of at least 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% as compared to the L-asparaginase when not conjugated to PEG. In another embodiment, the conjugate has an L-asparagine depletion activity at least about 10, 20, 30, 40, 50, 60, 70, 80, 90, or 100 times more potent than the L-asparaginase when not conjugated to PEG. In another embodiment, the conjugate depletes plasma L-asparagine levels to an undetectable level for at least about 12, 24, 48, 96, 108, or 120 hours.

In one embodiment, the conjugate has a longer in vivo circulating half life compared to the L-asparaginase when not conjugated to PEG. In a specific embodiment, the conjugate has a longer t½ than pegaspargase (i.e., PEG-conjugated L-asparaginase from *E. coli*) administered at an equivalent protein dose (e.g., measured in μg/kg). In a more specific embodiment, the conjugate has a t½ of at least about 58 to about 65 hours at a dose of about 50 μg/kg on a protein content basis, and a t½ of at least about 34 to about 40 hours at a dose of about 10 μg/kg on a protein content basis, following iv administration in mice. In another specific embodiment, the conjugate has a t½ of at least about 100 to about 200 hours at a dose ranging from about 10,000 to about 15,000 IU/m2 (about 20-30 mg protein/m2). In one embodiment, the conjugate has a greater area under the curve (AUC) compared to the L-asparaginase when not conjugated to PEG. In a specific embodiment, the conjugate has a mean AUC that is at least about 3 times greater than pegaspargase at an equivalent protein dose.

In one embodiment, the PEG is covalently linked to one or more amino groups (wherein "amino groups" includes lysine residues and/or the N-terminus) of the L-asparaginase. In a more specific embodiment, the PEG is covalently linked to the one or more amino groups by an amide bond. In another specific embodiment, the PEG is covalently linked to at least from about 40% to about 100% of the accessible amino groups (e.g., lysine residues and/or the N-terminus of the protein) or at least from about 40% to about 90% of total amino groups (e.g., lysine residues and/or the N-terminus of the protein). In one embodiment, the conjugate has the formula:

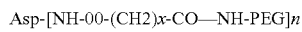

Asp-[NH-00-(CH2)x-CO—NH-PEG]n wherein Asp is the L-asparaginase, NH is one or more of the NH groups of the lysine residues and/or the N-terminus of the Asp, PEG is a polyethylene glycol moiety, n is a number that represents at least about 40% to about 100% of the accessible amino groups (e.g., lysine residues and/or the N-terminus) in the Asp, and x is an integer ranging from about 1 to about 8, more specifically, from about 2 to about 5. In a specific embodiment, the PEG is monomethoxypolyethylene glycol (mPEG).

In another aspect, the invention is directed to a method of making a conjugate comprising combining an amount of PEG with an amount of the L-asparaginase in a buffered solution for a time period sufficient to covalently link the PEG to the L-asparaginase.

In another aspect, the invention is directed to a pharmaceutical composition comprising the conjugate of the invention.

In another aspect, the invention is directed to a method of treating a disease treatable by L-asparagine depletion in a patient comprising administering an effective amount of the conjugate of the invention. In one embodiment, the disease is a cancer. In a specific embodiment, the cancer is ALL. In another specific embodiment, the conjugate is administered at an amount of about 5 U/kg body weight to about 50 U/kg body weight. In another specific embodiment, the conjugate is administered at a dose ranging from about 10,000 to about 15,000 IU/m2 (about 20-30 mg protein/m2). In some embodiments, the administration may be intravenous or intramuscular and may be less than once per week (e.g., once per month or once every other week), once per week, twice per week, or three times per week. In other specific embodiments, the conjugate is administered as monotherapy and, more specifically, without an asparagine synthetase inhibitor. In other embodiments, the conjugate is administered as part of a combination therapy (but in some embodiments, the combination therapy does not comprise an asparagine synthetase inhibitor). In a specific embodiment, the patient receiving treatment has had a previous hypersensitivity to an *E. coli* asparaginase or PEGylated form thereof or to an *Erwinia* asparaginase. In another specific embodiment, the patient receiving treatment has had a disease relapse, in particular a relapse that occurs after treatment with an *E. coli* asparaginase or PEGylated form thereof.

BRIEF DESCRIPTION OF THE DRAWINGS/FIGURES

FIG. 1: SDS-polyacrylamide gel electrophoresis of purified recombinant *Erwinia chrysanthemi* L-asparaginase. Purified recombinant *Erwinia chrysanthemi* L-asparaginase (r-crisantaspase) was analyzed on SDS-PAGE. Protein bands were stained with silver nitrate. Lane 1: Molecular Weight Marker (116, 66.2, 45, 35, 25, 18.4, and 14.4 kDa), lane 2: purified recombinant *Erwinia chrysanthemi* L-asparaginase (r-crisantaspase).

Figure 2:
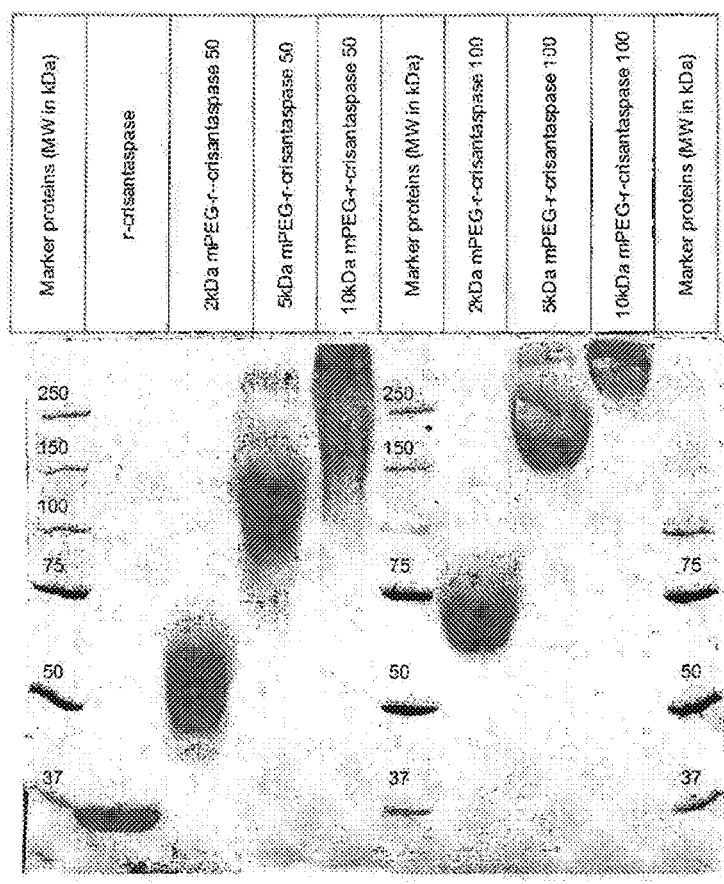

FIG. 2: SDS-PAGE analysis of mPEG-r-crisantaspase conjugates.

Figure 3:
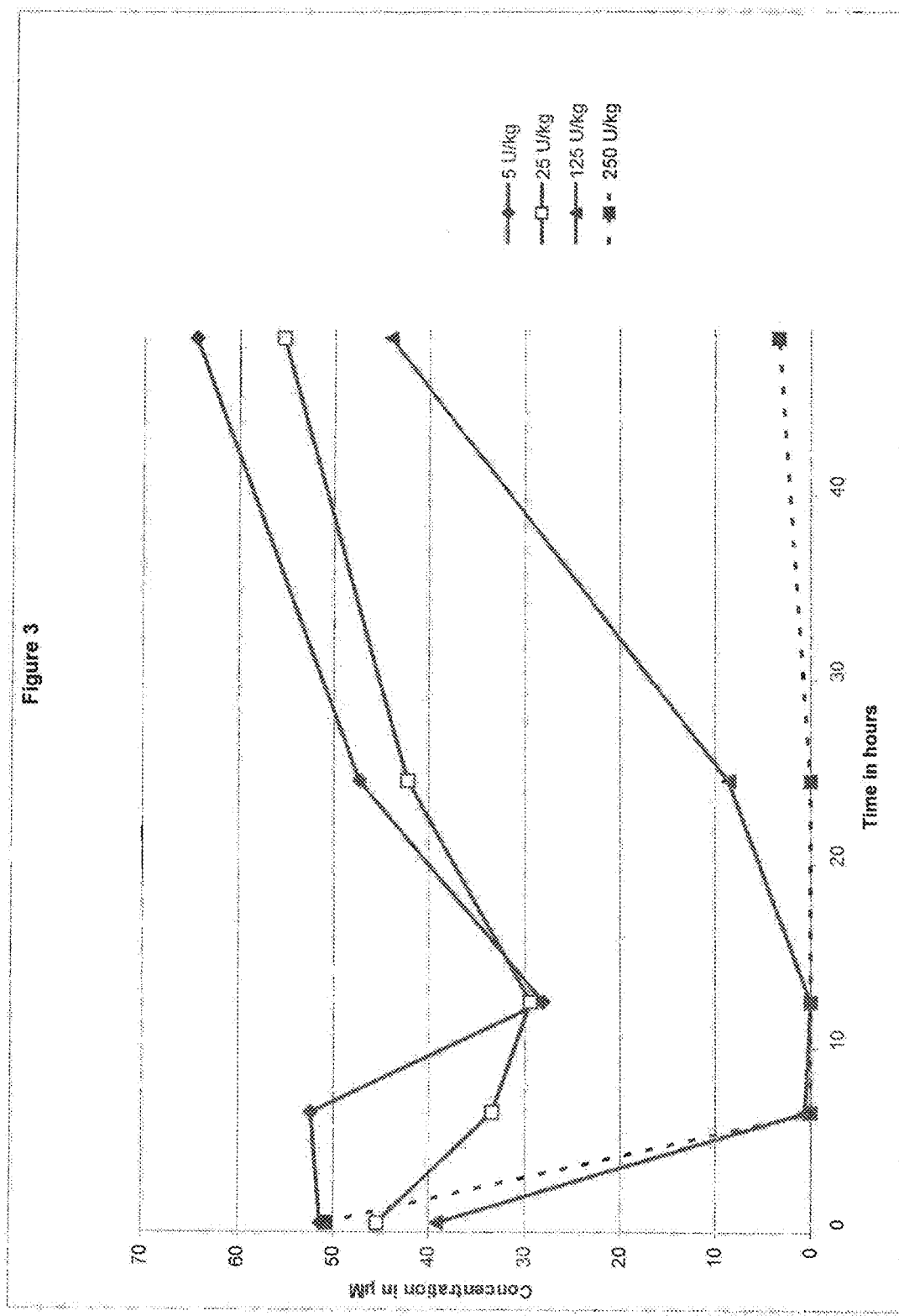

FIG. 3: Plasma L-asparagine levels following a single intravenous dose of Erwinase® (5 U/kg, 25 U/kg, 125 U/kg and 250 U/kg body weight).

Figure 4:
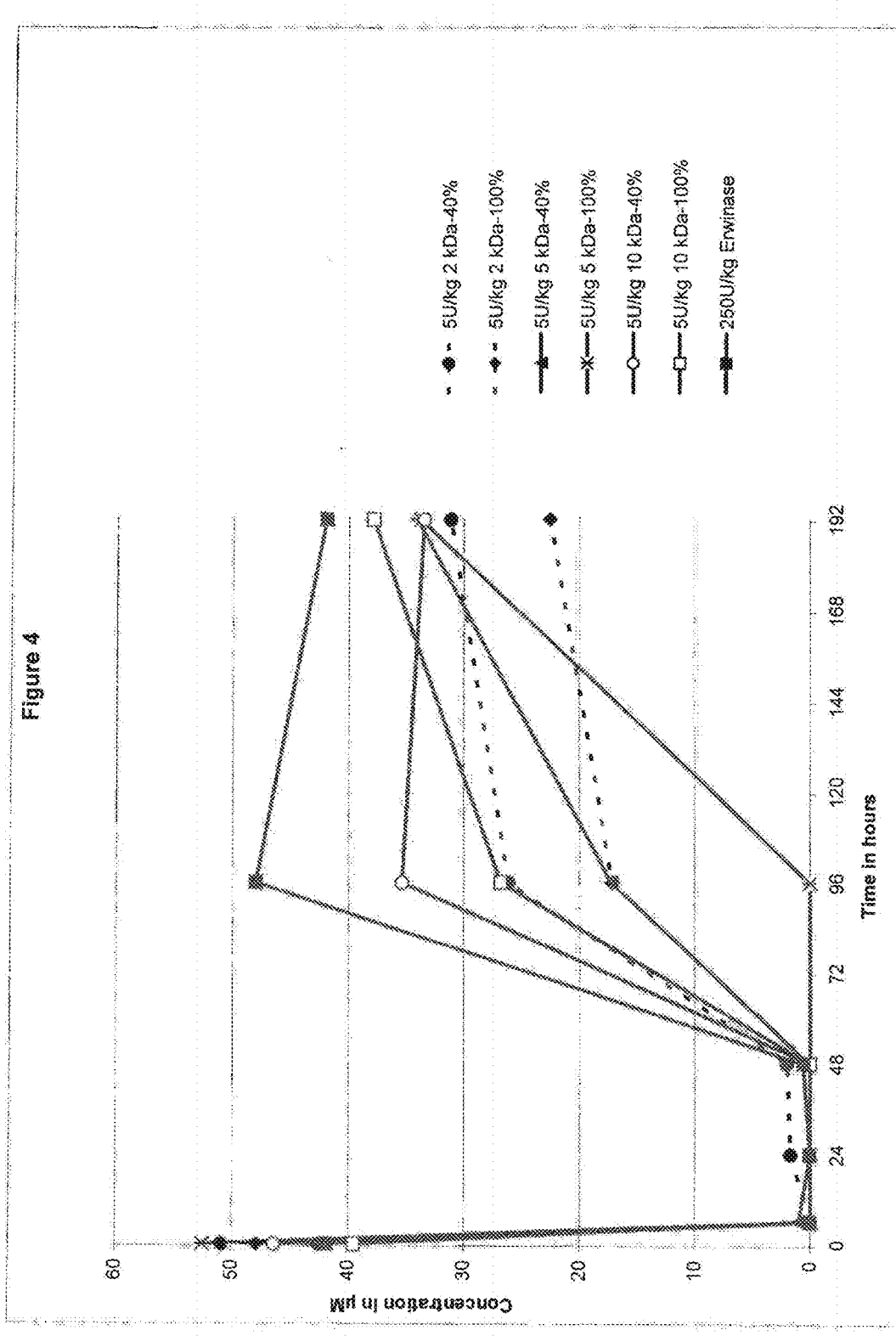

FIG. 4: Plasma L-asparagine levels following a single intravenous injection of mPEG-r-crisantaspase conjugates compared to Erwinase® in mice. The numbers "40%" and "100%" indicate an approximate degree of PEGylation of, respectively, about 40-55% (partially PEGylated) and about 100% (maximally PEGylated) of the accessible amino groups.

Figure 5:
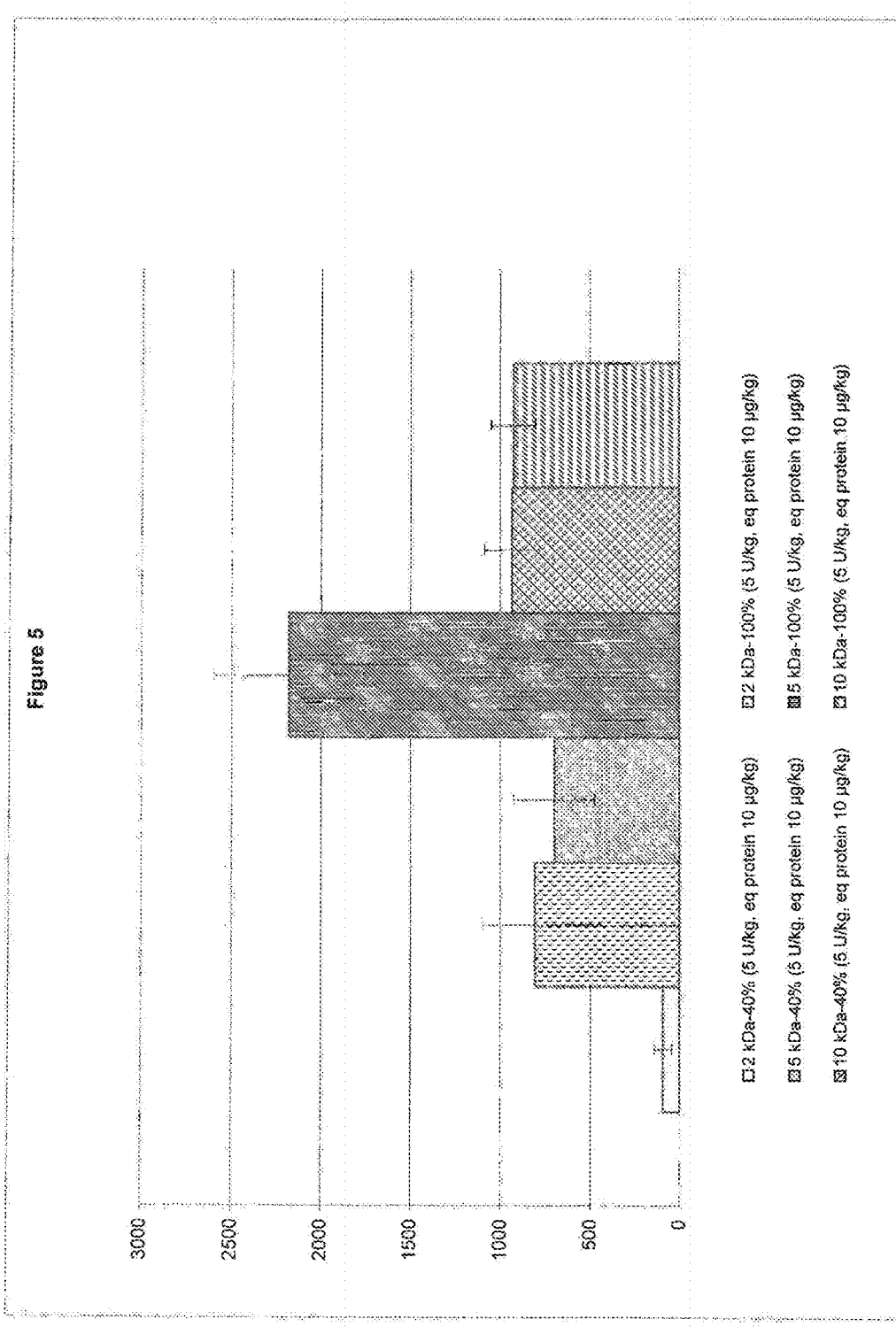

FIG. 5: Area under the curves (AUC) (residual enzymatic activity) calculated from L-asparaginase profiles following a single intravenous injection of mPEG-r-crisantaspase conjugates in mice.

Figure 6C:
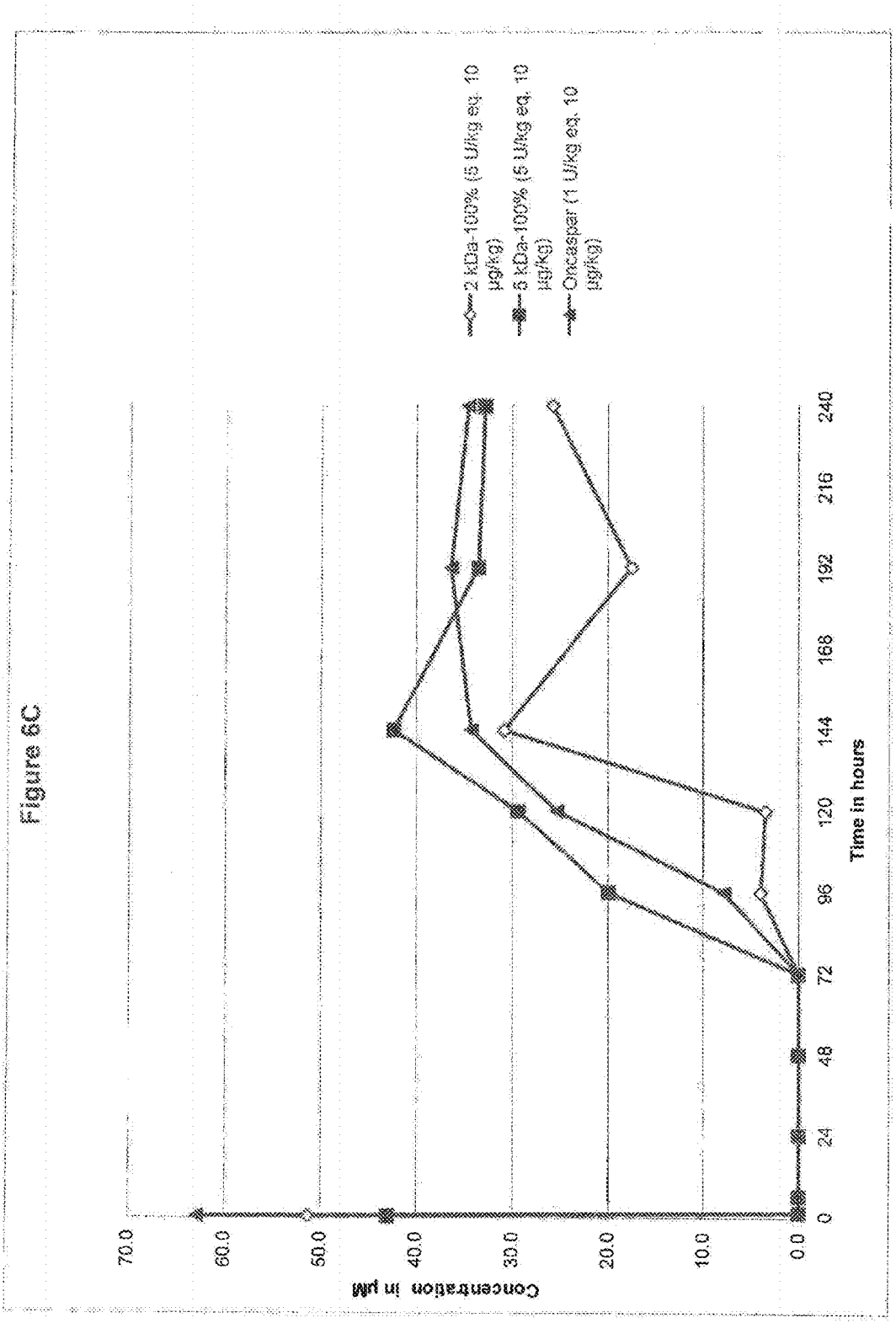

FIGS. 6A, 6B and 6C: Plasma L-asparagine levels following a single intravenous dose in mice of 2 kDa-100% mPEG-r-crisantaspase (5 U/kg, 25 U/kg and 50 U/kg body weight) (FIG. 6A), 5 kDa-100% mPEG-r-crisantaspase (5 U/kg, 25 U/kg and 50 U/kg body weight) (FIG. 6B), or 2 kDa-100% mPEG-r-crisantaspase (5 U/kg), 5 lcD a-100% mPEG-r-crisantaspase (5 U/kg), and pegaspargase (Oncaspar®) (1 U/kg) (FIG. 6C). Administration of an equivalent quantity of protein (10 μg/kg) of either 2 kDa-100% mPEG-r-crisantaspase (5 U/kg), 5 kDa-100% mPEG-r-crisantaspase (5 U/kg), or pegaspargase (Oncaspar®, 1 U/kg), resulted in a similar L-asparagine depletion over 72 hours.

Figure 7B:
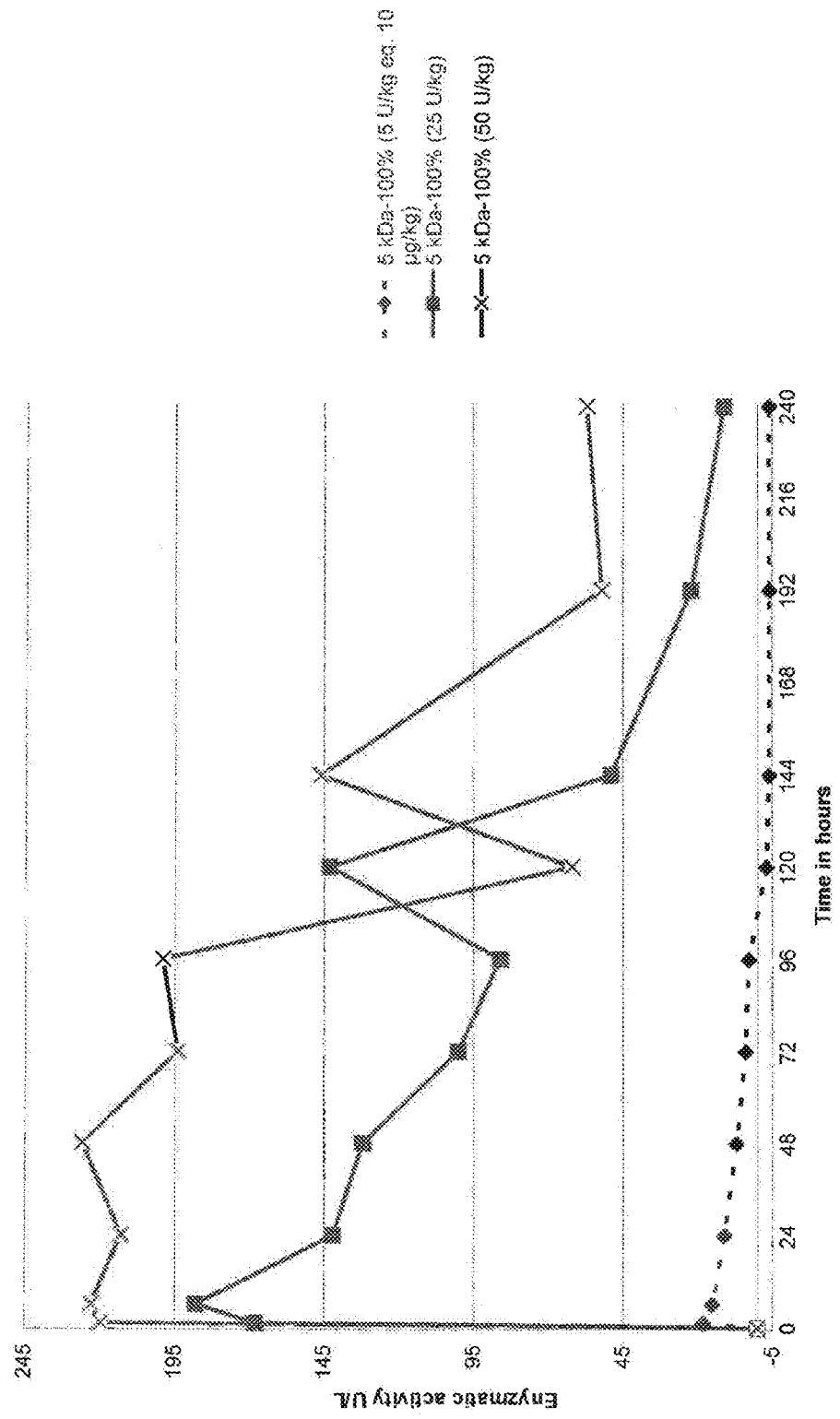

FIGS. 7A and 7B: Dose-effect Relationship of 2 kDa-100% PEGylated r-crisantaspase compared to 5 kDa-100% PEGylated r-crisantaspase. FIG. 7A shows the residual enzymatic activity in plasma following a single intravenous dose of 2 kDa-100% PEGylated r-crisantaspase at 5 U/kg (10 m/kg on a protein content basis), 25 U/kg, and 50 U/kg. FIG. 7B shows the residual enzymatic activity in plasma following a single intravenous dose of 5 kDa-100% PEGylated r-crisantaspase at 5 U/kg (10 m/kg on a protein content basis), 25 U/kg, and 50 U/kg.

FIG. 8: Dose-effect relationship of 2 kDa-100% PEGylated r-crisantaspase compared to 5 kDa-100% PEGylated r-crisantaspase. AUCs of the residual enzymatic activity measured in mice after a single intravenous dose of 2 kDa-100% or 5 kDa-100% mPEG-conjugates. Overall, when compared at the same dose level, AUCs measured for the 5 kDa-100% mPEG-r-crisantaspase were higher than those observed for the 2-kDa-100% mPEG-r-crisantaspase. A difference of 31, 37, and 14% was observed at 5, 25, and 50 U/kg doses, respectively.

FIGS. 9A and 9B: Pharmacokinetics of mPEG-r-crisantaspase conjugates vs. pegaspargase (Oncaspar®) in mice. FIG. 9A represents the residual enzymatic activity measured in mice after a single intravenous dose of 2 kDa-100% mPEG-r-crisantaspase, 5 kDa-100% mPEG-r-crisantaspase, or pegaspargase (Oncaspar®). FIG. 9B represents AUCs of the residual enzymatic activity measured in mice after a single intravenous dose of 2 kDa-100% mPEG-r-crisantaspase, 5 kDa-100% mPEG-r-crisantaspase, or pegaspargase (Oncaspar®).

FIG. 10: Serum levels of anti-crisantaspase specific antibodies after treatment with mPEG-r-crisantaspase conjugates or Erwinase®. Antibodies are directed toward crisantaspase. Data are expressed as means±SD (N=8).

FIGS. 11A and 11B: Serum levels of anti-conjugate specific antibodies after treatment with mPEG-r-crisantaspase maximally (100%) PEGylated conjugates. FIG. 11A: results presented as mean+SD (n=8); FIG. 11B: results presented as the percentage of animals with absorbance values >0.5 in the anti-conjugate ELISA.

DETAILED DESCRIPTION OF THE INVENTION

In one aspect, the problem to be solved by the invention is to provide an L-asparaginase preparation with:
High in vitro bioactivity;
A stable PEG-protein linkage;
Prolonged in vivo half-life;
Significantly reduced immunogenicity, as evidenced, for example, by the reduction or elimination of an antibody response against the L-asparaginase preparation following repeated administrations; and
Usefulness as a second-line therapy for patients who have developed sensitivity to first-line therapies using, e g, *E. coli*-derived L-asparaginases.

This problem has not been solved by known L-asparaginase conjugates, which either have significant cross-reactivity with modified L-asparaginase preparations (Wang, B. et. al (2003) *Leukemia* 17, 1583-1588, incorporated herein by reference in its entirety), or which have considerably reduced in vitro activity (Kuchumova, A. V. et. al (2007) *Biochemistry* (Moscow) Supplement Series B: Biomedical Chemistry, 1, 230-232, incorporated herein by reference in its entirety). This problem is solved according to the present invention by providing a conjugate of *Erwinia* L-asparaginase with a hydrophilic polymer, more specifically, a polyethylene glycol with a molecular weight of 5000 Da or less, a method for preparing such a conjugate and the use of the conjugate.

Described herein is a PEGylated L-asparaginase from *Erwinia* with improved pharmacological properties as compared with the unmodified L-asparaginase protein, as well as compared to the pegaspargase preparation from *E. coli*. The PEGylated L-asparaginase conjugate described herein, e.g., *Erwinia chrysanthemi* L-asparaginase PEGylated with 5000 Da molecular weight PEG, serves as a therapeutic agent particularly for use in patients who show hypersensitivity (e.g., an allergic reaction or silent hypersensitivity) to treatment with L-asparaginase or PEGylated L-asparaginase from *E. coli*. or unmodified L-asparaginase from *Erwinia*. The PEGylated L-asparaginase conjugate described herein is also useful as a therapeutic agent for use in patients who have had a disease relapse, e.g., a relapse of ALL, and have been previously treated with another form of asparaginase, e.g., with L-asparaginase or PEGylated L-asparaginase from *E. coli*.

As described in detail herein, the conjugate of the invention shows unexpectedly superior properties compared to known L-asparaginase preparations such as pegaspargase. For example, unmodified L-asparaginase from *Erwinia chrysanthemi* (crisantaspase) has a significantly lower half-life than unmodified L-asparaginase from *E. coli* (Avramis and Panosyan, Clin. Pharmacokinet. (2005) 44:367-393, incorporated herein by reference in its entirety). The PEGylated conjugate of the invention has a half life that is greater than PEGylated L-asparaginase from *E. coli* at an equivalent protein dose.

Definitions

Unless otherwise expressly defined, the terms used herein will be understood according to their ordinary meaning in the art.

As used herein, the term "including" means "including, without limitation," and terms used in the singular shall include the plural, and vice versa, unless the context dictates otherwise.

As used herein, the term "disease treatable by depletion of asparagine" refers to a condition or disorder wherein the cells involved in or responsible for the condition or disorder either lack or have a reduced ability to synthesize L-asparagine. Depletion or deprivation of L-asparagine can be partial or substantially complete (e.g., to levels that are undetectable using methods and apparatus that are known in the art).

As used herein, the term "therapeutically effective amount" refers to the amount of a protein (e.g., asparaginase or conjugate thereof), required to produce a desired therapeutic effect.

L-Asparaginase Protein

The protein according to the invention is an enzyme with L-asparagine aminohydrolase activity, namely an L-asparaginase.

Many L-asparaginase proteins have been identified in the art, isolated by known methods from microorganisms. (See, e.g., Savitri and Azmi, Indian *J. Biotechnol* 2 (2003) 184-194, incorporated herein by reference in its entirety). The most widely used and commercially available L-asparaginases are derived from *E. coli* or from *Erwinia chrysanthemi*, both of which share 50% or less structural homology. Within the *Erwinia* species, typically 75-77% sequence identity was reported between *Erwinia chrysanthemi* and *Erwinia carotovora*-derived enzymes, and approximately 90% sequence identity was found between different subspecies of *Erwinia chrysanthemi* (Kotzia G A, Labrou E, Journal of Biotechnology (2007) 127:657-669, incorporated herein by reference in its entirety). Some representative *Erwinia* L-asparaginases include, for example, those provided in Table 1:

TABLE 1

| SPECIES | GENBANK ACCESSION No. | % IDENTITY TO *ERWINIA CHRYSANTHEMI* NCPPB 1066 |
|---|---|---|
| *Erwinia chrysanthemi* 3937 | AAS67028 | 91% |
| *Erwinia chrysanthemi* NCPPB 1125 | CAA31239 | 98% |
| *Erwinia carotovora* subsp. *Astrosceptica* | AAS67027 | 75% |
| *Erwinia carotovora* | AAP92666 | 77% |

The sequences of the *Erwinia* L-asparaginases and the GenBank entries of Table 1 are herein incorporated by reference. Preferred L-asparaginases used in therapy are L-asparaginase isolated from *E. coli* and from *Erwinia*, specifically, *Erwinia chrysanthemi*.

The L-asparaginases may be native enzymes isolated from the microorganisms. They can also be produced by recombinant enzyme technologies in producing microorganisms such as *E. coli*. As examples, the protein used in the conjugate of the invention can be a protein form *E. coli* produced in a recombinant *E. coli* producing strain, of a protein from an *Erwinia* species, particularly *Erwinia chrysanthemi*, produced in a recombinant *E. coli* producing strain.

Enzymes can be identified by their specific activities. This definition thus includes all polypeptides that have the defined specific activity also present in other organisms, more particularly in other microorganisms. Often enzymes with similar activities can be identified by their grouping to certain families defined as PFAM or COG. PFAM (protein family database of alignments and hidden Markov models; pfam.sanfferac.ukl) represents a large collection of protein sequence alignments. Each PFAM makes it possible to visualize multiple alignments, see protein domains, evaluate distribution among organisms, gain access to other data-bases, and visualize known protein structures. COGs (Clusters of Orthologous Groups of proteins; vv-ww.nebi.nlm.nih.gov/COG/) are obtained by comparing protein sequences from 43 fully sequenced genomes representing 30 major phylogenetic lines. Each COG is defined from at least three lines, which permits the identification of former conserved domains.

The means of identifying homologous sequences and their percentage homology and/or identity are well known to those skilled in the art, and include in particular the BLAST programs, which can be used from the website blast.ncbi.nlm.nih.gov/Blast.cgi with the default parameters indicated on that website. The sequences obtained can then be exploited (e.g., aligned) using, for example, the programs CLUSTALW (www.ebi.ac.uk/Tools/clustalw2/index.html) or MULTALIN (bioinfo.genotoul.fr/multalin/multalin.html) with the default parameters indicated on those websites. Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook. et. al (1989 MOLECULAR CLONING: A LABORATORY MANUAL. 2nd ed. Cold Spring Harbor Lab., Cold Spring Harbor, N.Y.).

Indeed, a person skilled in the art will understand how to select and design homologous proteins retaining substantially their L-asparaginase activity. Typically, a Nessler assay is used for the determination of L-asparaginase activity according to a method described by Mashburn and Wriston (Mashburn, L., and Wriston, J. (1963) "Tumor Inhibitory Effect of L-Asparaginase," Biochem Biophys Res Commun 12, 50, incorporated herein by reference in its entirety).

In a particular embodiment of the conjugate of the invention, the L-asparaginase protein has at least about 80% homology or identity with the protein comprising the sequence of SEQ ID NO:1, more specifically at least about 85%, 86%, 87%, 88%, 89%, 90%, 91%, 92%, 93%, 94%, 95%, 96%, 97%, 98%, 99%, or 100% homology or identity with the protein comprising the sequence of SEQ ID NO: 1. SEQ ID NO: 1 is as follows:

(SEQ ID NO: 1)
ADKLPNIVILATGGTIAGSAATGTQTTGYKAGALGVDTLINAVPEVKKLA

NVKGEQFSNMASENMTGDVVLKLSQRVNELLARDDVDGVVITHGTDTVEE

SAYFLHLTVKSDKPVVFVAAMRPATAISADGPMNLLEAVRVAGDKQSRGR

GVMVVLNDRIGSARYITKTNASTLDTFKANEEGYLGVIIGNRIYYQNRID

KLHTTRSVFDVRGLTSLPKVDILYGYQDDPEYLYDAAIQHGVKGIVYAGM

GAGSVSVRGIAGMRKAMEKGVVVIRSTRTGNGIVPPDEELPGLVSDSLNP

AHARILLMLALTRTSDPKVIQEYFHTY

The term "comprising the sequence of SEQ ID NO: 1" means that the amino-acid sequence of the protein may not be strictly limited to SEQ ID NO: 1 but may contain additional amino-acids.

In a particular embodiment, the protein is the L-asparaginase of Erwinia chrysanthemi having the sequence of SEQ ID NO: 1. In another embodiment, the L-asparaginase is from Erwinia chrysanthemi NCPPB 1066 (Genbank Accession No. CAA32884, incorporated herein by reference in its entirety), either with or without signal peptides and/or leader sequences.

Fragments of the protein of SEQ ID NO: 1 are also comprised within the definition of the protein used in the conjugate of the invention. The term "a fragment of SEQ ID NO: 1—means that the sequence of the polypeptide may include less amino-acid than SEQ ID NO1 but still enough amino-acids to confer L-aminohydrolase activity.

It is well known in the art that a polypeptide can be modified by substitution, insertion, deletion and/or addition of one or more amino-acids while retaining its enzymatic activity. For example, substitution of one amino-acid at a given position by a chemically equivalent amino-acid that does not affect the functional properties of a protein is common. Substitutions may be defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: His, Arg, Lys

Large aliphatic, non-polar residues: Met, Leu, Ile, Val, Cys

Large aromatic residues: Phe, Tyr, Trp.

Thus, changes that result in the substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids subject to modification in the amino-acid sequence are not particularly limited. The skilled artisan is able to recognize the modifications that can be introduced without affecting the activity of the protein. For example, modifications in the N- or C-terminal portion of a protein may be expected not to alter the activity of a protein under certain circumstances. With respect to asparaginases, in particular, much characterization has been done, particularly with respect to the sequences, structures, and the residues forming the active catalytic site. This provides guidance with respect to residues that can be modified without affecting the activity of the enzyme. All known L-asparaginases from bacterial sources have common structural features. All are homotetramers with four active sites between the N- and C-terminal domains of two adjacent monomers (Aghaipour et. al, Biochemistry 40 (2001) 5655-5664, incorporated herein by reference in its entirety). All have a high degree of similarity in their tertiary and quaternary structures (Papageorgiou et. al, FEBS J. 275 (2008) 4306-4316, incorporated herein by reference in its entirety). The sequences of the catalytic sites of L-asparaginases are highly conserved between Erwinia chrysanthemi, Erwinia carotovora, and E. coli L-asparaginase II (Papageorgiou et. al, FEBS J. 275 (2008) 4306-4316). The active site flexible loop contains amino acid residues 14-33, and structural analysis show that Thr15, Thr95, Ser62, Glu63, Asp96, and Ala120 contact the ligand (Papageorgiou et al., FEBS J. 275 (2008) 4306-4316). Aghaipour et. al have conducted a detailed analysis of the four active sites of Erwinia chrysanthemi L-asparaginase by examining high resolution crystal structures of the enzyme complexed with its substrates (Aghaipour et. al, Biochemistry 40 (2001) 5655-5664). Kotzia et. al provide sequences for L-asparaginases from several species and subspecies of Erwinia and, even though the proteins have only about 75-77% identity between *Erwinia chrysanthemi* and *Erwinia carotovora*, they each still have L-asparaginase activity (Kotzia et. al, *J. Biotechnol.* 127 (2007) 657-669, incorporated herein by reference in its entirety). Moola et. al performed epitope mapping studies of *Erwinia chrysanthemi* 3937 L-asparaginase and were able to retain enzyme activity even after mutating various antigenic sequences in an attempt to reduce immunogenicity of the asparaginase (Moola et. al, *Biochem*. J. 302 (1994) 921-927, incorporated herein by reference in its entirety). Each of the above-cited articles is herein incorporated by reference in its entirety. In view of the extensive characterization that has been performed on L-asparaginases, one of skill in the art could determine how to make fragments and/or sequence substitutions while still retaining enzyme activity.

Polymers for Use in the Conjugate

Polymers are selected from the group of non-toxic water soluble polymers such as polysaccharides, e.g. hydroxyethyl starch, poly amino acids, e.g. poly lysine, polyester, e.g., polylactic acid, and poly alkylene oxides, e.g., polyethylene glycol (PEG).

Polyethylene glycol (PEG) or mono-methoxy-polyethyleneglycol (mPEG) is well known in the art and comprises linear and branched polymers. Examples of some polymers, particularly PEG, are provided in the following, each of which is herein incorporated by reference in its entirety: U.S. Pat. Nos. 5,672,662; 4,179,337; 5,252,714; US Pat. Appl. Publ. No. 2003/0114647; U.S. Pat. Nos. 6,113,906; 7,419,600; and PCT Publ. No. WO2004/083258.

The quality of such polymers is characterized by the polydispersity index (PDI). The PDI reflects the distribution of molecular weights in a given polymer sample and is calculated from the weight average molecular weight divided by the number average molecular weight. It indicates the distribution of individual molecular weights in a batch of polymers. The PDI has a value always greater than 1, but as the polymer chains approach the ideal Gauss distribution (=monodispersity), the PDI approaches 1.

The polyethylene glycol has advantageously a molecular weight comprised within the range of about 500 Da to about 9,000 Da. More specifically, the polyethylene glycol (e.g, mPEG) has a molecular weight selected from the group consisting of polyethylene glycols of 2000 Da, 2500 Da, 3000 Da, 3500 Da, 4000 Da, 4500 Da, and 5000 Da. In a particular embodiment, the polyethylene glycol (e.g., mPEG) has a molecular weight of 5000 Da.

Method for Preparing the Conjugate

For subsequent coupling of the polymer to proteins with L-asparagine aminohydrolase activity, the polymer moiety contains an activated functionality that preferably reacts with amino groups in the protein. In one aspect, the invention is directed to a method of making a conjugate, the method comprising combining an amount of polyethylene glycol (PEG) with an amount of L-asparaginase in a buffered solution for a time period sufficient to covalently link the PEG to the L-asparaginase. In a particular embodiment, the L-asparaginase is from *Erwinia* species, more specifically *Erwinia chrysanthemi*, and more specifically, the L-asparaginase comprising the sequence of SEQ ID NO: 1. In one embodiment, the PEG is monomethoxy-polyethylene glycol (mPEG).

In one embodiment, the reaction between the polyethylene glycol and L-asparaginase is performed in a buffered solution. In some particular embodiments, the pH value of the buffer solution ranges between about 7.0 and about 9.0. The most preferred pH value ranges between about 7.5 and about 8.5, e.g., a pH value of about 7.5, 7.6, 7.7, 7.8, 7.9, 8.0, 8.1, 8.2, 8.3, 8.4, or 15 8.5. In a particular embodiment, the L-asparaginase is from *Erwinia* species, more specifically *Erwinia chrysanthemi*, and more specifically, the L-asparaginase comprising the sequence of SEQ ID NO: 1.

Furthermore, PEGylation of L-asparaginase is performed at protein concentrations between about 0.5 and about 25 mg/mL, more specifically between about 2 and about 20 mg/mL and most specifically between about 3 and about 15 mg/mL. For example, the protein concentration is about 0.5, 1, 2, 3, 4, 5, 6, 7, 8, 9, 10, 11, 12, 13, 14, 15, 16, 17, 18, 19, or 20 mg/mL. In a particular embodiment, the PEGylation of L-asparaginase at these protein concentrations is of *Erwinia* species, more specifically *Erwinia chrysanthemi*, and more specifically, the L-asparaginase comprising the sequence of SEQ ID NO: 1.

At elevated protein concentration of more than 2 mg/mL the PEGylation reaction proceeds rapidly, within less than 2 hours. Furthermore, a molar excess of polymer over amino groups in L-asparaginase of less than about 20:1 is applied. For example, the molar excess is less than about 20:1, 19:1, 18:1, 17:1, 16:1, 15:1, 14:1, 13:1, 12:1, 11:1, 10:1, 9:1, 8:1, 7.5:1, 7:1, 6.5:1, 6:1, 5.5:1, 5:1, 4.5:1, 4:1, 3.5:1, 3:1, 2.5:1, 2:1, 1.5:1, or 1:1. In a specific embodiment the molar excess is less than about 10:1 and in a more specific embodiment, the molar excess is less than about 8:1. In a particular embodiment, the L-asparaginase is from *Erwinia* species, more specifically *Erwinia chrysanthemi*, and more specifically, the L-asparaginase comprising the sequence of SEQ ID NO: 1.

The number of PEG moieties which can be coupled to the protein will be subject to the number of free amino groups and, even more so, to which amino groups are accessible for a PEGylation reaction. In a particular embodiment, the degree of PEGylation (i.e., the number of PEG moieties coupled to amino groups on the L-asparaginase) is within a range from about 10% to about 100% of free and/or accessible amino groups (e.g., about 10%, 15%, 20%, 25%, 30%, 40%, 50%, 60%, 70%, 80%, 90%, or 100%). 100% PEGylation of accessible amino groups (e.g., lysine residues and/or the N-terminus of the protein) is also referred to herein as "maximally PEGylated." One method to determine the modified amino groups in mPEG-r-crisantaspase conjugates (degree of PEGylation) is a method described by Habeeb (A. F. S. A. Habeeb, "Determination of free amino groups in proteins by trinitrobenzensulfonic acid", Anal. Biochem. 14 (1966), p. 328, incorporated herein by reference in its entirety). In one embodiment, the PEG moieties are coupled to one or more amino groups (wherein amino groups include lysine residues and/or the N-terminus) of the L-asparaginase. In a particular embodiment, the degree of PEGylation is within a range of from about 10% to about 100% of total or accessible amino groups (e.g., lysine residues and/or the N-terminus), e.g., about 10%, 15%, 20%, 25%, 30%, 35%, 40%, 45%, 50%, 55%, 60%, 65%, 70%, 75%, 80%, 85%, 90%, 95% or 100%. In a specific embodiment, about 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the total amino groups (e.g., lysine residues and/or the N-terminus) are coupled to a PEG moiety. In another specific embodiment, about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 70%, 71%, 72%, 7%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the accessible amino groups (e.g., lysine residues and/or the N-terminus) are coupled to a PEG moiety. In a specific embodiment, 40-55% or 100% of the accessible amino groups (e.g., lysine residues and/or the N-terminus) are coupled to a PEG moiety. In some embodiments, the PEG moieties are coupled to the L-asparaginase by a covalent linkage. In a particular embodiment, the L-asparaginase is from *Erwinia* species, more specifically *Erwinia chrysanthemi*, and more specifically, the L-asparaginase comprising the sequence of SEQ ID NO: 1.

In one embodiment, the conjugate of the invention can be represented by the formula

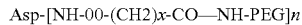

wherein Asp is a L-asparaginase protein, NH is the NH group of a lysine residue and/or the N-terminus of the protein chain, PEG is a polyethylene glycol moiety and n is a number of at least 40% to about 100% of the accessible amino groups (e.g., lysine residues and/or the N-terminus) in the protein, all being defined above and below in the examples, x is an integer ranging from 1 to 8 (e.g., 1, 2, 3, 4, 5, 6, 7, 8), preferably 2 to 5 (e.g., 2, 3, 4, 5). In a particular embodiment, the L-asparaginase is from *Erwinia* species, more specifically *Erwinia chrysanthemi*, and more specifically, the L-asparaginase comprising the sequence of SEQ ID NO: 1.

Other methods of PEGylation that can be used to form the conjugates of the invention are provided, for example, in U.S. Pat. Nos. 4,179,337, 5,766,897, U.S. Pat. Appl. Publ. No. US 2002/0065397A1, and U.S. Pat. Appl. Publ. No. US 2009/0054590A1, each of which is herein incorporated by reference in its entirety.

Specific embodiments include proteins having substantial L-Asparagine aminohydrolase activity and polyethylene glycol, selected from the group of conjugates wherein:

(A)
the protein has at least 90% homology of structure with the L-asparaginase from *Erwinia chrysanthemi* as disclosed in SEQ ID NO: 1
the polyethylene glycol has a molecular weight of about 5000 Da,
the protein and polyethylene glycol moieties are covalently linked to the protein by amide bonds, and
about 100% of the accessible amino groups (e.g., lysine residues and/or the N-terminus) or about 80-90%, in particular, about 84%, of total amino groups (e.g., lysine residues and/or the N-terminus) are linked to a polyethylene glycol moiety.

(B)
the protein has at least 90% homology with the L-asparaginase from *Erwinia chrysanthemi* as disclosed in SEQ ID NO: 1
the polyethylene glycol has a molecular weight of about 5000 Da,
the protein and polyethylene glycol moieties are covalently linked to the protein by amide bonds, and
about 40% to about 45%, and in particular about 43% of the accessible amino groups (e.g., lysine residues and/or the N-terminus), or about 36% of the total amino groups (e.g., lysine residues and/or the N-terminus) are linked to a polyethylene glycol moiety.

(C)
the protein has at least 90% homology with the L-asparaginase from *Erwinia chrysanthemi* as disclosed in SEQ ID NO: 1
the polyethylene glycol has a molecular weight of about 2000 Da,
the protein and polyethylene glycol moieties are covalently linked to the protein by amide bonds, and
about 100% of the accessible amino groups (e.g., one or more lysine residues and/or the N-terminus) or about 80-90%, in particular, about 84% of total amino groups (e.g., lysine residues and/or the N-terminus) are linked to a polyethylene glycol moiety.

(D)
the protein has at least 90% homology with the L-asparaginase from *Erwinia chrysanthemi* as disclosed in SEQ ID NO:1
the polyethylene glycol has a molecular weight of about 2000 Da, the protein and polyethylene glycol moieties are covalently linked to the protein by amide bonds, and
about 50% to about 60%, and in particular about 55% of the accessible amino groups (e.g., lysine residues and/or the N-terminus) or about 47% of the total amino groups (e.g., lysine residues and/or the N-terminus) are linked to a polyethylene glycol moiety.

L-Asparaginase-PEG Conjugates

Conjugates of the invention have certain advantageous and unexpected properties compared to unmodified L-asparaginases, particularly compared to unmodified *Erwinia* L-asparaginases, more particularly compared to unmodified L-asparaginase from *Erwinia chrysanthemi*, and more particularly compared to unmodified L-asparaginase having the sequence of SEQ ID NO: 1.

In some embodiments, the conjugate of the invention reduces plasma L-asparagine levels for a time period of at least about 12, 24, 48, 72, 96, or 120 hours when administered at a dose of 5 U/kg body weight (bw) or 10 µg/kg (protein content basis). In other embodiments, the conjugate of the invention reduces plasma L-asparagine levels to undetectable levels for a time period of at least about 12, 24, 48, 72, 96, 120, or 144 hours when administered at a dose of 25 U/kg bw or 50 µg/kg (protein content basis). In other embodiments, the conjugate of the invention reduces plasma L-asparagine levels for a time period of at least about 12, 24, 48, 72, 96, 120, 144, 168, 192, 216, or 240 hours when administered at a dose of 50 U/kg bw or 100 µg/kg (protein content basis). In another embodiment, the conjugate of the invention reduces plasma L-asparagine levels to undetectable levels for a time period of at least about 12, 24, 48, 72, 96, 120, 144, 168, 192, 216, or 240 hours when administered at a dose ranging from about 10,000 to about 15,000 IU/m2 (about 20-30 mg protein/m2). In a particular embodiment, the conjugate comprises L-asparaginase from *Erwinia* species, more specifically *Erwinia chrysanthemi*, and more specifically, the L-asparaginase comprising the sequence of SEQ ID NO: 1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-terminus) are PEGylated.

In one embodiment, the conjugate comprises a ratio of mol PEG/mol monomer of about 4.5 to about 8.5, particularly about 6.5; a specific activity of about 450 to about 550 U/mg, particularly about 501 U/mg; and a relative activity of about 75% to about 85%, particularly about 81% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 40-55% accessible amino groups (e.g., lysine residues and/or the N-terminus) with 5000 Da mPEG.

In one embodiment, the conjugate comprises a ratio of mol PEG/mol monomer of about 12.0 to about 18.0, particularly about 15.1; a specific activity of about 450 to about 550 U/mg, particularly about 483 U/mg; and a relative activity of about 75 to about 85%, particularly about 78% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 100% accessible amino groups (e.g., lysine residues and/or the N-terminus) with 5000 Da mPEG.

In one embodiment, the conjugate comprises a ratio of mol PEG/mol monomer of about 5.0 to about 9.0, particularly about 7.0; a specific activity of about 450 to about 550 U/mg, particularly about 501 U/mg; and a relative activity of about 80 to about 90%, particularly about 87% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 40-55% accessible amino groups (e.g., lysine residues and/or the N-terminus) with 10,000 Da mPEG.

In one embodiment, the conjugate comprises a ratio of mol PEG/mol monomer of about 11.0 to about 17.0, particularly about 14.1; a specific activity of about 450 to about 550 U/mg, particularly about 541 U/mg; and a relative activity of about 80 to about 90%, particularly about 87% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 100% accessible amino groups (e.g., lysine residues and/or the N-terminus) with 10,000 Da mPEG.

In one embodiment, the conjugate comprises a ratio of mol PEG/mol monomer of about 6.5 to about 10.5, particularly about 8.5; a specific activity of about 450 to about 550 U/mg, particularly about 524 U/mg; and a relative activity of about 80 to about 90%, particularly about 84% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 40-55% accessible amino groups (e.g., lysine residues and/or the N-terminus) with 2,000 Da mPEG.

In one embodiment, the conjugate comprises a ratio of mol PEG/mol monomer of about 12.5 to about 18.5, particularly about 15.5; a specific activity of about 450 to about 550 U/mg, particularly about 515 U/mg; and a relative activity of about 80 to about 90%, particularly about 83% compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1, with PEGylation of approximately 100% accessible amino groups (e.g., lysine residues and/or the N-terminus) with 2,000 Da mPEG.

In other embodiments, the conjugate of the invention has an increased potency of at least about 10 times, 20 times, 30 times, 40 times, 50 times, 60 times, 70 times, 80 times, 90 times, or 100 times after a single injection compared to the corresponding unmodified L-asparaginase. In a specific embodiment, the conjugate with these properties comprises an L-asparaginase from *Erwinia* species, more specifically *Erwinia chrysanthemi*, and more specifically, the L-asparaginase comprising the sequence of SEQ ID NO: 1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-terminus) are PEGylated.

In one aspect the conjugate of the invention has a pharmacokinetic profile according to the following parameters:

| Parameter | Definition |
| --- | --- |
| $A_{max}$ | Maximal residual enzyme activity |
| $t_{Amax}$ | Time to Amax after test item exposure |
| $d_{Amax}$ | Maximal duration of Amax or A above zero |

The half-life time of the residual enzyme activity in plasma is derived from the following formula:

$$\text{Mean: } t_{1/2} = \frac{-\ln 2 \times t}{\ln(c_t / c_0)}$$

where t½ is the half-life, t is the time point, ct is the residual plasma activity at the time point and co the residual plasma activity at the beginning. Area under the curve (AUC) is calculated using a pharmacokinetics software program, e.g., SigmaPlot Version1 1.

In one embodiment, the conjugate of the invention has a single-dose pharmacokinetic profile according to the following, specifically wherein the conjugate comprises mPEG at molecular weight of less than or equal to 2000 Da and an L-asparaginase from *Erwinia* species, more specifically *Erwinia chrysanthemi*, and more specifically, the L-asparaginase comprising the sequence of SEQ ID NO:1:

$A_{max}$: about 150 U/L to about 250 U/L;
$T_{Amax}$: about 4 h to about 8 h, specifically about 6 h;
$d_{Amax}$: about 220 h to about 250 h, specifically, about 238.5 h (above zero, from about 90 min to about 240 h);
AUC: about 12000 to about 30000; and
t½: about 50 h to about 90 h.

In one embodiment, the conjugate of the invention has a single-dose pharmacokinetic profile according to the following, specifically where the conjugate comprises mPEG at molecular weight of less than or equal to 5000 Da and an L-asparaginase from *Erwinia* species, more specifically *Erwinia chrysanthemi*, and more specifically, the L-asparaginase comprising the sequence of SEQ ID NO:1:

$A_{max}$: about 18 U/L to about 250 U/L;
$T_{Amax}$: about 1 h to about 50 h;
$d_{Amax}$: about 90 h to about 250 h, specifically, about 238.5 h (above zero, from about 90 min to about 240 h);
AUC: about 500 to about 35000; and
t½: about 30 h to about 120 h.

In one embodiment, the conjugate of the invention results in a similar level of L-asparagine depletion over a period of time (e.g., 24, 48, or 72 hours) after a single dose compared to an equivalent quantity of protein of pegaspargase. In a specific embodiment, the conjugate comprises an L-asparaginase from *Erwinia* species, more specifically *Erwinia chrysanthemi*, and more specifically, the L-asparaginase comprising the sequence of SEQ ID NO:1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-terminus) are PEGylated, more particularly about 40-55% or 100%.

In one embodiment, the conjugate of the invention has a longer tu2 than pegaspargase administered at an equivalent protein dose. In an a specific embodiment, the conjugate has a t½ of at least about 50, 52, 54, 56, 58, 59, 60, 61, 62, 63, 64, or 65 hours at a dose of about 50 µg/kg (protein content basis). In another specific embodiment, the conjugate has a t½ of at least about 30, 32, 34, 36, 37, 38, 39, or 40 hours at a dose of about 10 µg/kg (protein content basis). In another specific embodiment, the conjugate has a tlp of at least about 100 to about 200 hours at a dose ranging from about 10,000 to about 15,000 IU/m2 (about 20-30 mg protein/m2).

In one embodiment, the conjugate of the invention has a mean AUC that is at least about 2, 3, 4 or 5 times greater than pegaspargase at an equivalent protein dose.

In one embodiment, the conjugate of the invention does not raise any significant antibody response for a particular period of time after administration of a single dose, e.g, greater than about 1 week, 2 weeks, 3 weeks, 4, weeks, 5 weeks, 6 weeks, 7 weeks, 8 weeks, 9 weeks, 10 weeks, 11 weeks, 12 weeks, etc. In a particular embodiment the conjugate of the invention does not raise any significant antibody response for at least 8 weeks. In one example, "does not raise any significant antibody response" means that the subject receiving the conjugate is identified within art-recognized parameters as "antibody-negative." Antibody levels can be determined by methods known in the art, for example ELISA or surface plasmon resonance (SPR-Biacore) assays (Zalewska-Szewczyk et. al, Clin. Exp. Med. (2009) 9:113-116; Avramis et. al, Anticancer Research 29 (2009) 299-302, each of which is incorporated herein by reference in its entirety). Conjugates of the invention may have any combination of these properties.

Methods of Treatment and Use of the Conjugate

The conjugates of the invention can be used in the treatment of a disease treatable by depletion of asparagine. For example, the conjugate is useful in the treatment or the manufacture of a medicament for use in the treatment of acute lymphoblastic Leukemia (ALL) in both adults and children, as well as other conditions where asparagine depletion is expected to have a useful effect. Such conditions include, but are not limited to the following: malignancies, or cancers, including but not limited to hematalogic malignancies, non-Hodgkin's lymphoma, NK lymphoma, pancreatic cancer, Hodgkin's disease, acute myelocytic Leukemia, acute myelomonocytic Leukemia, chronic lymphocytic Leukemia, lymphosarcoma, reticulosarcoma, and melanosarcoma. Representative non-malignant hematologic diseases which respond to asparagine depletion include immune system-mediated Blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, AIDS, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. Cells suspected of causing disease can be tested for asparagine dependence in any suitable in vitro or in vivo assay, e.g., an in vitro assay wherein the growth medium lacks asparagine. Thus, in one aspect, the invention is directed to a method of treating a disease treatable in a patient, the method comprising administering to the patient an effective amount of a conjugate of the invention. In a specific embodiment, the disease is ALL. In a particular embodiment, the conjugate used in the treatment of a disease treatable by asparagine depletion comprises an L-asparaginase from *Erwinia* species, more specifically *Erwinia chrysanthemi*, and more specifically, the L-asparaginase comprising the sequence of SEQ ID NO:1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-terminus) are PEGylated, more particularly about 40-55% or 100%.

In one embodiment, treatment with a conjugate of the invention will be administered as a first line therapy. In another embodiment, treatment with a conjugate of the invention will be administered as a second line therapy in patients, particularly patients with ALL, where objective signs of allergy or hypersensitivity, including "silent hypersensitivity," have developed to other asparaginase preparations, in particular, the native *Escherichia-coli*-derived L-asparaginase or its PEGylated variant (pegaspargase). Non-limiting examples of objective signs of allergy or hypersensitivity include testing "antibody positive" for an asparaginase enzyme. In a specific embodiment, the conjugate of the invention is used in second line therapy after treatment with pegaspargase. In a more specific embodiment, the conjugate used in second line therapy comprises an L-asparaginase from *Erwinia* species, more specifically *Erwinia chrysanthemi*, and more specifically, the L-asparaginase comprising the sequence of SEQ ID NO:1. In a more specific embodiment, the conjugate further comprises PEG (e.g., mPEG) having a molecular weight of less than or equal to about 5000 Da, more specifically about 5000 Da. In an even more specific embodiment, at least about 40% to about 100% of accessible amino groups (e.g., lysine residues and/or the N-terminus) are PEGylated, more particularly about 40-55% or 100%.

In another aspect, the invention is directed to a method for treating acute lymphoblastic Leukemia comprising administering to a patient in need of the treatment a therapeutically effective amount of a conjugate of the invention. In a specific embodiment, treatment will be administered at a dose ranging from about 1500 IU/m$^2$ to about 15,000 IU/m$^2$, typically about 10,000 to about 15,000 IU/m2 (about 20-30 mg protein/m$^2$), at a schedule ranging from about twice a week to about once a month, typically once per week or once every other week, as a single agent (e.g., monotherapy) or as part of a combination of chemotherapy drugs, including, but not limited to glucocorticoids, corticostcroids, anticancer compounds or other agents, including, but not limited to methotrexate, dexamethasone, prednisone, prednisolone, vincristine, cyclophosphamide, and anthracycline. As an example, patients with ALL will be administered the conjugate of the invention as a component of multi-agent chemotherapy during 3 chemotherapy phases including induction, consolidation or intensification, and maintenance. In a specific example, the conjugate is not administered with an asparagine synthetase inhibitor (e.g., such as set forth in PCT Pub. No. WO 2007/103290, which is herein incorporated by reference in its entirety). In another specific example, the conjugate is not administered with an asparagine synthetase inhibitor, but is administered with other chemotherapy drugs. The conjugate can be administered before, after, or simultaneously with other compounds as part of a multi-agent chemotherapy regimen. In a particular embodiment, the conjugate comprises L-asparaginase from *Erwinia* species, more specifically *Erwinia chrysanthemi*, and more specifically, the L-asparaginase comprising the sequence of SEQ ID NO:1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-terminus) are PEGylated, more particularly about 40-55% or 100%.

In a specific embodiment, the method comprises administering a conjugate of the invention at an amount of about 1 U/kg to about 25 U/kg (e.g., about 1, 2, 3, 4, 5, 6, 7, 8, 9, 10, 11, 12, 13, 14, 15, 16, 17, 18, 19, 20, 21, 22, 23, 24, or 25 U/kg) or an equivalent amount thereof 20 (e.g., on a protein content basis). In a more specific embodiment, the conjugate is administered at an amount selected from the group consisting of about 5, about 10, and about 25 U/kg. In another specific embodiment, the conjugate is administered at a dose ranging from about 1,000 IU/m2 to about 20,000 IU/m 2 (e.g., 1,000 IU/m², 2,000 IU/m², 3,000 IU/m², 4,000 IU/m², 5,000 IU/m², 6,000 IU/m², 7,000 IU/m², 8,000 IU/m², 9,000 IU/m², 10,000 IU/m², 11,000 IU/m², 25 12,000 IU/m², 13,000 IU/m², 14,000 IU/m², 15,000 IU/m², 16,000 IU/m², 17,000 IU/m², 18,000 IU/m², 19,000 IU/m², or 20,000 IU/m²). In another specific embodiment, the conjugate is administered at a dose that depletes L-asparagine to undetectable levels using methods and apparatus known in the art for a period of about 3 days to about 10 days (e.g., 3, 4, 5, 6, 7, 8, 9, or 10 days) for a single dose. In another embodiment, the method comprises administering a conjugate of the invention that elicits a lower immunogenic response in a patient compared to an unconjugated L-asparaginase. In another embodiment, the method comprises administering a conjugate of the invention that has a longer in vivo circulating half-life after a single dose compared to the unconjugated L-asparaginase. In one embodiment, the method comprises administering a conjugate that has a longer t½ than pegaspargase administered at an equivalent protein dose. In an a specific embodiment, the method comprises administering a conjugate that has a t½ of at least about 50, 52, 54, 56, 58, 59, 60, 61, 62, 63, 64, or 65 hours at a dose of about 50 µg/kg (protein content basis). In another specific embodiment, the method comprises administering a conjugate that has a t½ of at least about 30, 32, 34, 36, 37, 37, 39, or 40 hours at a dose of about 10 µg/kg (protein content basis). In another specific embodiment, the method comprises administering a conjugate that has a t½ at least about 100 to about 200 hours at a dose ranging from about 10,000 to about 15,000 IU/m² (about 20-30 mg protein/m²). In one embodiment, the method comprises administering a conjugate that has a mean AUC that is at least about 2, 3, 4 or 5 times greater than pegaspargase at an equivalent protein dose. In another embodiment, the method comprises administering a conjugate of the invention that has a greater AUC value after a single dose compared to the unconjugated L-asparaginase. In a particular embodiment, the conjugate comprises L-asparaginase from *Erwinia* species, more specifically *Erwinia chrysanthemi*, and more specifically, the L-asparaginase comprising the sequence of SEQ ID NO: 1. In a particular embodiment, the conjugate comprises PEG (e.g., mPEG) having a molecular weight of less than or equal to about 5000 Da. In a more particular embodiment, at least about 40% to about 100% of accessible amino groups (e.g., lysine residues and/or the N-15 terminus) are PEGylated, more particularly about 40-55% or 100%.

The incidence of relapse in ALL patients following treatment with L-asparaginase remains high, with approximately 10-25% of pediatric ALL patients having early relapse (e.g., some during maintenance phase at 30-36 months post-induction) (Avramis and Panosyan, Clin. Pharmacokinet. (2005) 44:367-393). If a patient treated with *E. coli*-derived L-asparaginase has a relapse, subsequent treatment with *E. coli* preparations could lead to a "vaccination" effect, whereby the *E. coli* preparation has increased immunogenicity during the subsequent administrations. In one embodiment, the conjugate of the invention may be used in a method of treating patients with relapsed ALL who were previously treated with other asparaginase preparations, in particular those who were previously treated with *E. coli*-derived asparaginases.

In some embodiments, the uses and methods of treatment of the invention comprise administering an L-asparaginase conjugate having properties or combinations of properties described herein above (e.g., in the section entitled "L-asparaginase PEG conjugates") or herein below.

Compositions, Formulations, and Routes of Administration

The invention also includes a pharmaceutical composition comprising a conjugate of the invention. In a specific embodiment the pharmaceutical composition is contained in a vial as a lyophilized powder to be reconstituted with a solvent, such as currently available native L-asparaginases, whatever the bacterial source used for its production (Kidrolase®, Elspar®, Erwinase® . . . ). In another embodiment, the pharmaceutical composition is a "ready to use" solution, such as pegaspargase (Oncaspar®) enabling, further to an appropriate handling, an administration through, e.g., intramuscular, intravenous (infusion and/or bolus), intra-cerebro-ventricular (icv), subcutaneous routes.

Conjugates of the invention, including compositions comprising conjugates of the invention (e.g., a pharmaceutical composition) can be administered to a patient using standard techniques. Techniques and formulations generally may be found in Remington's Pharmaceutical Sciences, 18th ed., Mack Publishing Co., Easton, Pa., 1990 (herein incorporated by reference).

Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the Blood stream preferably are soluble.

Conjugates and/or pharmaceutical compositions according to the invention can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of an asparaginase may be present as a complex, as those in the art will appreciate.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-to luenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, supra. Such salts can be prepared using the appropriate corresponding bases.

Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose.

Pharmaceutical compositions according to the invention can be administered by different routes, including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops.

Alternatively, injection (parenteral administration) may be used, e.g., intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the conjugate can be produced. In a specific embodiment, the conjugate is administered intramuscularly. In another specific embodiment, the conjugate is administered intravenously.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories.

For topical administration, compounds can be formulated into ointments, salves, gels, or creams, as is well known in the art.

The amounts of the conjugate to be delivered will depend on many factors, for example, the $IC_{50}$, $EC_{50}$, the biological half-life of the compound, the age, size, weight, and physical condition of the patient, and the disease or disorder to be treated. The importance of these and other factors to be considered are well known to those of ordinary skill in the art. Generally, the amount of the conjugate to be administered will range from about 10 International Units per square meter of the surface area of the patient's body ($IU/m^2$) to 50,000 $IU/m^2$, with a dosage range of about 1,000 $IU/m^2$ to about 15,000 $IU/m^2$ being preferred, and a range of about 6,000 $IU/m^2$ to about 15,000 $IU/m^2$ being more preferred, and a range of about 10,000 to about 15,000 $IU/m^2$ (about 20-30 mg protein/$m^2$) being particularly preferred to treat a malignant hematologic disease, e.g., Leukemia. Typically, these dosages are administered via intramuscular or intravenous injection at an interval of about 3 times weekly to about once per month, typically once per week or once every other week during the course of therapy. Of course, other dosages and/or treatment regimens may be employed, as determined by the attending physician.

In particular embodiments, the conjugate and/or pharmaceutical composition or formulation to be administered as described herein comprises L-asparaginase from *Erwinia* species, more specifically *Erwinia chrysanthemi*, and more specifically, the L-asparaginase comprising the sequence of SEQ ID NO:1. In a particular embodiment, the conjugate comprises L-asparaginase from *Erwinia* species, more specifically *Erwinia chrysanthemi*, and more specifically, the L-asparaginase comprising the sequence of SEQ ID NO: 1. In a particular embodiment, the conjugate comprises PEG (e.g., mPEG) having a molecular weight of less than or equal to about 5000 Da. In a more particular embodiment, at least about 40% to about 100% of amino groups (e.g., lysine residues and/or the N-terminus) are PEGylated.

EXAMPLES

Example 1

Preparation of Recombinant Crisantaspase

The recombinant bacterial strain used to manufacture the naked recombinant *Erwinia chrysanthemi* L-asparaginase protein (also referred to herein as "r-crisantaspase") was an *E. coli* BL21 strain with a deleted ansB gene (the gene encoding the endogenous *E. coli* type 11 L-asparaginase) to avoid potential contamination of the recombinant *Erwinia chrysanthemi* L-asparaginase with this enzyme. The deletion of the ansB gene relies on homologous recombination methods and phage transduction performed according to the three following steps: 1) a bacterial strain (NM1100) expressing a defective lambda phage which supplies functions that protect and recombine electroporated linear DNA substrate in the bacterial cell was transformed with a linear plasmid (kanamycin cassette) containing the kanamycin gene flanked by an FLP recognition target sequence (FRT). Recombination occurs to replace the ansB gene by the kanamycin cassette in the bacterial genome, resulting in a ansB strain; 2) phage transduction was used to integrate the integrated kanamycin cassette region from the zlansB NM1100 strain to the ansB locus in BL21 strain. This results in an *E. coli* BL21 strain with a deleted ansB gene and resistant to kanamycin; 3) this strain was transformed with a FLP-helper plasmid to remove the kanamycin gene by homologous recombination at the FRT sequence. The genome of the final strain (BL21 ΔansB strain) was sequenced, confirming full deletion of the endogenous ansB gene.

The *E. coli*-optimized DNA sequence encoding for the mature *Erwinia chrysanthemi* L-asparaginase fused with the ENX signal peptide from *Bacillus subtilis* was inserted into an expression vector. This vector allows expression of recombinant *Erwinia chrysanthemi* L-asparaginase under the control of hybrid T5/lac promoter induced by the addition of Isopropyl 13-D-1-thiogalactopyranoside (IPTG) and confers resistance to kanamycin.

BL21 ΔansB strain was transformed with this expression vector. The transformed cells were used for production of the r-crisantaspase by feed batch glucose fermentation in Reisenberg medium. The induction of the cell was done 16 h at 23° C. with IPTG as inducer. After cell harvest and lysis by homogenization in 10 mM sodium phosphate buffer pH6 5 mM EDTA (Buffer A), the protein solution was clarified by centrifugation twice at 15000 g, followed by 0.45 jtm and 0.22 jtm filtration steps. The recombinant *Erwinia chrysanthemi* L-asparaginase was next purified using a sequence of chromatography and concentration steps. Briefly, the theoretical isoelectric point of the *Erwinia chrysanthemi* L-asparaginase (7.23) permits the recombinant enzyme to adsorb to cation exchange resins at pH6. Thus, the recombinant enzyme was captured on a Capto S column (cation exchange chromatography) and eluted with salt gradient in Buffer A. Fractions containing the recombinant enzyme were pooled. The pooled solution was next purified on Capto MMC column (cation exchange chromatography) in Buffer A with salt gradient. The eluted fractions containing *Erwinia chrysanthemi* L-asparaginase were pooled and concentrated before protein separation on Superdex 200 pg size exclusion chromatography as polishing step. Fractions containing recombinant enzymes were pooled, concentrated, and diafiltered against 100 mM sodium phosphate buffer pH8. The purity of the final *Erwinia chrysanthemi* L-asparaginase preparation was evaluated by SDS-PAGE (FIG. 1) and RP-HPLC and was at least 90%. The integrity of the recombinant enzyme was verified by N-terminal sequencing and LC-MS. Enzyme activity was measured at 37° C. using Nessler's reagent. The specific activity of the purified recombinant *Erwinia chrysanthemi* L-asparaginase was around 600 U/mg. One unit of enzyme activity is defined as the amount of enzyme that liberates ljunol of ammonia from L-asparagine per minute at 37° C.

Example 2

Preparation of 10 kDa mPEG-L-Asparaginase Conjugates

A solution of L-asparaginase from *Erwinia chrysanthemi* was stirred in a 100 mM sodium phosphate buffer at pH 8.0, at a protein concentration between 2.5 and 4 mg/mL, in the presence of 150 mg/mL or 36 mg/mL 10 kDa mPEG-NHS, for 2 hours at 22° C. The resulting crude 10 kDa mPEG-L-asparaginase was purified by size exclusion chromatography using a Superdex 200 pg column on an Akta purifier UPC 100 system. Protein-containing fractions were pooled and concentrated to result in a protein concentration between 2 and 8 mg/mL. Two 10 kDa mPEG-L-asparaginase conjugates were prepared in this way, differing in their degree of PEGylation as determined by TNBS assay with unmodified L-asparaginase as a reference, one corresponding to full PEGylation (100% of accessible amino groups (e.g., lysine residues and/or the N-terminus) residues being conjugated corresponding to PEGylation of 78% of total amino groups (e.g., lysine residues and/or the N-terminus)); the second one corresponding to partial PEGylation (39% of total amino groups (e.g., lysine residues and/or the N-terminus) or about 50% of accessible amino groups (e.g., lysine residues and/or the N-terminus)). SDS-PAGE analysis of the conjugates is shown in FIG. 2. The resulting conjugates appeared as an essentially homogeneous band and contained no detectable unmodified r-crisantaspase.

Example 3

Preparation of 5 kDa mPEG-L-Asparaginase Conjugates

A solution of L-asparaginase from *Erwinia chrysanthemi* was stirred in a 100 mM sodium phosphate buffer at pH 8.0, at a protein concentration of 4 mg/mL, in the presence of 150 mg/mL or 22.5 mg/mL 5 kDa mPEG-NHS, for 2 hours at 22° C. The resulting crude 5 kDa mPEG-L-asparaginase was purified by size exclusion chromatography using a Superdex 200 pg column on an Akta purifier UPC 100 system. Protein-containing fractions were pooled and concentrated to result in a protein concentration between 2 and 8 mg/mL. Two 5 kDa mPEG-L-asparaginase conjugates were prepared in this way, differing in their degree of PEGylation as determined by TNBS assay with unmodified L-asparaginase as a reference, one corresponding to full PEGylation (100% of accessible amino groups (e.g., lysine residues and/or the N-terminus) being conjugated corresponding to PEGylation of 84% of total amino groups (e.g., lysine residues and/or the N-terminus)); the second one corresponding to partial PEGylation (36% of total amino groups (e.g., lysine residues and/or the N-terminus) or about 43% of accessible amino groups (e.g., lysine residues and/or the N-terminus)). SDS-PAGE analysis of the conjugates is shown in FIG. 2. The resulting conjugates appeared as an essentially homogeneous band and contained no detectable unmodified r-crisantaspase.

Example 4

Preparation of 2 kDa mPEG-L-Asparaginase Conjugates

A solution of L-asparaginase from *Erwinia chrysanthemi* was stirred in a 100 mM sodium phosphate buffer pH 8.0 at a protein concentration of 4 mg/mL in the presence of 150 mg/mL or 22.5 mg/mL 2 kDa mPEG-NHS for 2 hours at 22° C. The resulting crude 2 kDa mPEG-L-asparaginase was purified by size exclusion chromatography using a Superdex 200 pg column on an Akta purifier UPC 100 system. Protein containing fractions were pooled and concentrated to result in a protein concentration between 2 and 8 mg/mL. Two 2 kDa mPEG-L-asparaginase conjugates were prepared in this way, differing in their degree of PEGylation as determined by TNBS assay with unmodified L-asparaginase as reference, one corresponding to maximum PEGylation (100% of accessible amino groups (e.g., lysine residues and/or the N-terminus) being conjugated corresponding to PEGylation of 86% of total amino groups (e.g., lysine residues and/or the N-terminus)); the second one corresponding to partial PEGylation (47% of total amino groups (e.g., lysine residues and/or the N-terminus) or about 55% of accessible amino groups (e.g., lysine residues and/or the N-terminus)). SDS- PAGE analysis of the conjugates is shown in FIG. 2. The resulting conjugates appeared as an essentially homogeneous band and contained no detectable unmodified r-crisantaspase.

Example 5

Activity of mPEG-r-Crisantaspase Conjugates

L-asparaginase aminohydrolase activity of each conjugate described in the proceeding examples was determined by Nesslerization of ammonia that is liberated from L-asparagine by enzymatic activity. Briefly, 50111_, of enzyme solution were mixed with 20 mM of L-asparagine in a 50 mM Sodium borate buffer pH 8.6 and incubated for 10 min at 37° C. The reaction was stopped by addition of 2001.iL of Nessler reagent. Absorbance of this solution was measured at 450 nm. The activity was calculated from a calibration curve that was obtained from Ammonia sulfate as reference. The results are summarized in Table 2, below:

TABLE 2

Activity of mPEG-r-crisantaspase conjugates

| Sample* | mol PEG/ mol monomer** | Specific activity [U/mg] | Rel. activity % |
|---|---|---|---|
| 10 kDa mPEG-r-crisantaspase 40% | 7.0 | 543 | 87 |
| 10 kDa mPEG-r-crisantaspase 100% | 14.1 | 541 | 87 |
| 5 kDa mPEG-r-crisantaspase 40% | 6.5 | 501 | 81 |
| 5 kDa mPEG-r-crisantaspase 100% | 15.1 | 483 | 78 |
| 2 kDa mPEG-r-crisantaspase 40% | 8.5 | 524 | 84 |
| 2 kDa mPEG-r-crisantaspase 100% | 15.5 | 515 | 83 |
| r-crisantaspase | — | 622 | 100 |

*the numbers "40%" and "100%" indicate an approximate degree of PEGylation of respectively 40-55% and 100% of accessible amino groups (see Examples 2-4, supra).
**the ratio mol PEG/mol monomer was extrapolated from data using TNBS assay, that makes the assumption that all amino groups from the protein (e.g., lysine residues and the N-terminus) are accessible.

Residual activity of mPEG-r-crisantaspase conjugates ranged between 483 and 543 Units/mg. This corresponds to 78-87% of L-asparagine aminohydrolase activity of the unmodified enzyme.

Example 6

L-Asparagine-Depleting Effect of Unmodified Crisantaspase

The pharmacodynamic profile of Erwinase® was determined in B6D2F1-Hybrids (immune competent, females), Charles River Germany. Erwinase® is a commercially available crisantaspase (L-asparaginase derived from *Erwinia chrysanthemi*). Briefly, 2 animals per group received a single i.v. injection of 5, 25, 125, or 250 Units/kg bw Erwinase® At −1 h pre-dose and at 6 h, 12 h, 24 h, and 48 h post-dose, plasma samples were collected from orbital sinus and analyzed for plasma levels of L-asparagine.

Plasma amino acid levels were determined with a PICO-TAG Amino Acid Analysis Kit (Waters). Briefly, plasma samples were deproteinised by methanol precipitation. Free amino acids in the supernatant were derivatised with phenylisothiocyanate and quantified by RP-HPLC.

As shown in FIG. 3, the 5 and 25 U/kg doses were not efficient in depleting L-asparagine levels in mice following iv administration. Only the 250 U/kg dose induced a complete depletion over 48 hrs.

This result illustrates the clinical limitations of Erwinase®, an unmodified crisantaspase, which needs to be administered up to 3 times a weeks as painful injections in patients suffering from ALL, and at high doses resulting in frequent allergic reactions and immunogenicity.

Example 7

L-Asparagine-Depleting Effect and Plasma L-Asparaginase Activity Following Single Administration of Six mPEG-r-Crisantaspase Conjugates The pharmacodynamic and pharmacokinetic profiles of 6 different mPEG-r-crisantaspase conjugates was determined in B6D2F1-Hybrids (immune competent, females), Charles River Germany The six conjugates tested differed in the molecular size of the PEG (2, 5 or 10 kDa) and in the degree of PEGylation (maximal vs. partial PEGylation). Unmodified crisantaspase (Erwinase®) was used as a reference. Briefly, 4 animals per group received a single i.v. injection of 5 Units/kg bw conjugate vs. 250 Units/kg bw Erwinase®. At −1 h pre-dose and at 6 h, 24 h, 48 h, 96 h and 192 h after injection, plasma samples were collected from the orbital sinus of each animal and analyzed for plasma levels of L-asparagine and residual enzyme activity, respectively.

Plasma amino acid levels were determined with a PICO-TAG Amino Acid Analysis Kit (Waters). Briefly, plasma samples were deproteinised by methanol precipitation. Free amino acids in the supernatant were derivatised with phenylisothiocyanate and quantified by RP-HPLC.

Enzyme activity in plasma was determined by a chromogenic assay. L-aspartic B-hydroxamate (AHA) was used as substrate. The enzymes hydrolyzed AHA to L-Asp and hydroxylamine, which was determined at 710 urn after condensation with 8-hydroxyquinoline and oxidation to indooxine. (Analytical *Biochemistry* 309 (2002): 117-126, incorporated herein by reference in its entirety).

As shown in FIG. 4, the, conjugates administered at 5 U/kg showed an L-asparagine depleting potency at least as good as that of Erwinase® 250 U/kg, suggesting that PEGylation increased potency of the protein by at least 50 times. All conjugates exhibited similar potency, depleting plasma levels in L-asparagine for 2 days, except for the 5 kDa-100% conjugate which showed longer duration of action (96 h=4 days as compared to 48 h=2 days for other conjugates).

Thus, increasing the size of the PEG conjugated to the r-crisantaspase from 2 kDa to 5 kDa resulted in an improved potency and duration of action. However, surprisingly, increasing the size of the PEG to 10 kDa did not further improve the potency and duration of action of the conjugate, it even resulted in a decrease when compared to the 5 kDa maximally PEGylated conjugate.

Enzymatic activity was consistent with L-asparagine depletion. As shown in FIG. 5, the 5 kDa-100% conjugate exhibited the largest AUC, reflecting a longer half-life. Lower AUCs were observed with PEG-40% (partially PEGylated) vs. PEG-100% (maximally PEGylated) conjugates for the 2 kDa and 5 kDa candidates and no difference was observed for the 10 kDa candidates.

Consistent with the L-asparagine depletion data, increasing the molecular size of the PEG conjugated to the r-crisantaspase from 2 kDa to 5 kDa resulted in a longer circulating L-asparaginase activity. However, surprisingly, increasing the size of the PEG to 10 kDa did not further improve the in vivo enzymatic activity of the conjugate, it even resulted in a decrease when compared to the 5 kDa maximally PEGylated conjugate. Also, notably, when r-crisantaspase was N-terminally monoPEGylated with high molecular weight (i.e., 40 kDa) mPEG, there was no significant impact on the in vitro stability of the enzyme toward proteolysis (data not shown).

Example 8

Dose-Ranging Effects of Two mPEG-r-Crisantaspase Conjugates on Plasma L-Asparagine The pharmacodynamic profile of 2 mPEG-r-crisantaspase conjugates compared to pegaspargase (Oncaspar®) was determined in B6D2F1-Hybrids (immune competent, females), Charles River Germany The conjugates tested were the 2 kDa maximally (100%) PEGylated r-crisantaspase and the 5 kDa maximally (100%) PEGylated r-crisantaspase at 3 doses. Briefly, 8 animals per group received a single i.v. injection of 5, 25 or 50 Units/kg bw of the r-crisantaspase conjugates, corresponding to 10, 50 or 100 lag protein/kg. As a comparative arm, Oncaspar® was tested at 1 Unit/kg, corresponding to 10 jig protein/kg. At −1 h pre-dose and at 90 min, 6 h, 24 h, 48 h, 72 h, 96 h, 120 h, 144 h, 192 h and 240 h post-dose plasma samples were collected from orbital sinus and analyzed for plasma levels of L-asparagine.

Plasma amino acid levels were determined with a PICO-TAG Amino Acid Analysis Kit (Waters). Briefly, plasma samples were deproteinised by methanol precipitation. Free amino acids in the supernatant were derivatised with phenylisothiocyanate and quantified by RP-HPLC.

The dose-related effects of the conjugates on plasma L-asparagine levels are shown in FIGS. 6A, 6B and 6C. As shown in FIGS. 6A and 6B, both conjugates were highly efficient in depleting circulating L-asparagine. For the 2 kDa 100% conjugate, total depletion was observed over 3, 6 and at least 10 days at the 5U, 25U and 50 U/kg doses, respectively. For the 5 kDa 100% conjugate, total depletion was observed over 3, 10 and 10 days at the 5U, 25U and 50 U/kg doses, respectively. For both conjugates tested, the 5, 25 and 50 U/kg doses tested corresponded to 10, 50 and 100 Kg/kg on a protein content basis, which is a very low amount of protein when compared to other available L-asparaginase preparations. Indeed, 250 U/kg Erwinase® corresponds to approximately 520 Kg/kg, and 1 U/kg Oncaspar® corresponds approximately to 10 [kg/kg (protein content basis). FIG. 6C shows that the administration of an equivalent quantity of protein (10 [kg/kg) of either the 2 kDa-100% conjugate, the 5 kDa-100% conjugate or Oncaspar® resulted in a similar L-asparagine depletion over 72 hrs.

Example 9

Pharmacokinetic Profiles of Two mPEG-r-Crisantaspase Conjugates

The pharmacokinetic profile of mPEG-r-crisantaspase conjugates was determined in B6D2F1-Hybrids (immune competent, females), Charles River Germany. The conjugates tested were the 2 kDa maximally (100%) PEGylated r-crisantaspase and the 5 kDa maximally (100%) fully PEGylated r-crisantaspase at 3 doses. Unmodified crisantaspase (Erwinase®) at 250 U/kg and Oncaspar® at 1 U/kg were also tested as controls. Briefly, 8 animals per group received a single i.v. injection of 5, 25 or 50 Units/kg bw of each mPEG-r-crisantaspase conjugate compared to Erwinase® and Oncaspar®. At −1 h pre-dose and at 90 min, 6 h, 24 h, 48 h, 72 h, 96 h, 120 h, 144 h, 192 h and 240 h post-dose plasma samples were collected from orbital sinus and analyzed for plasma levels of residual enzyme activity.

Enzyme activity in plasma was determined by a chromogenic assay. L-aspartic B-hydroxamate (AHA) was used as substrate. The enzymes hydrolyzed AHA to L-Asp and hydroxylamine, which was determined at 710 nm after condensation with 8-hydroxyquinoline and oxidation to indooxine. (*Analytical Biochemistry* 309 (2002): 117-126).

For the calculation of the half-life time, exponential best-fit lines of the respective residual plasma activities were derived using the MS-excel function tool. Negative activity values were excluded from the calculation.

| Parameter | Definition |
|---|---|
| $A_{max}$ | Maximal residual enzyme activity |
| $t_{Amax}$ | Time to $A_{max}$ after test item exposure |
| $d_{Amax}$ | Maximal duration of $A_{max}$ or A above zero |

The half-life time of the residual enzyme activity in plasma were derived from the following formula using the MS-excel function tool and the respective formula of the exponential best-fit lines:

$$\text{Mean: } t_{1/2} = \frac{-\ln 2 \times t}{\ln(c_t / c_0)}$$

where tuzis the half-life, t is the time point, c, is the residual plasma activity at the time point and co the residual plasma activity at the beginning.

The areas under the curve (AUC) were calculated using SigmaPlot Version1 1. Pharmacokinctic data arc summarized in Tables 3 and 4, below, and FIGS. 7A, 7B, 8, 9A and 9B.

TABLE 3

Primary pharmacokinetics of a single treatment with 250 U/kg bw of Erwinase ®, 1 U/kg bw Pegaspargase (Oncaspar ®), or 2 kDa mPEG-r-crisantaspase 100% conjugates (residual plasma enzyme activity)

| Parameter | Erwinase ® | Pegaspargase 1 U/kg bw | 2 kDa/ 100% 5 U/kg bw | 2 kDa/ 100% 25 U/kg bw | 2 kDa/ 100% 50 U/kg bw |
|---|---|---|---|---|---|
| $A_{max}$ | 83.9 U/L | 6 U/L | 14 U/L | 153 U/L | 208 U/L |
| $t_{Amax}$ | 6 h | 90 min | 90 min | 6 h | 6 h |
| $d_{Amax}$ | 18 h | 46.5 h | 70.5 h | 238.5 h | 238.5 h |
| above zero | from 6 h-24 h | 90 min-48 h | 90 min-72 h | 90 min-240 h | 90 min-240 h |

TABLE 3-continued

Primary pharmacokinetics of a single treatment with 250 U/kg bw of Erwinase ®, 1 U/kg bw Pegaspargase (Oncaspar ®), or 2 kDa mPEG-r-crisantaspase 100% conjugates (residual plasma enzyme activity)

| Parameter | Erwinase ® | Pegaspargase 1 U/kg bw | 2 kDa/ 100% 5 U/kg bw | 2 kDa/ 100% 25 U/kg bw | 2 kDa/ 100% 50 U/kg bw |
|---|---|---|---|---|---|
| AUC (mean) | 1205 | 222 | 627 | 12446 | 28349 |
| $t_{1/2}$ | 6 h | 28 h | 31 h | 55 h | 85 h |

TABLE 4

Primary pharmacokinetics of a single treatment with 250 U/kg bw of Erwinase ®, 1 U/kg bw Pegaspargase (Oncaspar ®), or 5 kDa mPEG-r-crisantaspase 100% conjugates (residual plasma enzyme activity)

| Parameter | Erwinase ® | Pegaspargase 1 U/kg bw | 5 kDa/ 100% 5 U/kg bw | 5 kDa/ 100% 25 U/kg bw | 5 kDa/ 100% 50 U/kg bw |
|---|---|---|---|---|---|
| $A_{max}$ | 83.9 U/L | 6 U/L | 18 U/L | 188 U/L | 226 U/L |
| $t_{Amax}$ | 6 h | 90 min | 90 min | 6 h | 6 h |
| $d_{Amax}$ above zero | 18 h from 6 h-24 h | 46.5 h 90 min-48 h | 94.5 h 90 min-72 h | 238.5 h 90 min-240 h | 238.5 h 90 min-240 h |
| AUC (mean) | 1205 | 222 | 798 | 19748 | 33151 |
| $t_{1/2}$ | 6 h | 28 h | 31 h | 55 h | 85 h |

The data show that PEGylation of r-crisantaspase significantly prolongs half-life when compared to unmodified crisantaspase, and in a dose-dependent manner (Tables 3 and 4, FIGS. 7A, 7B, 8, 9A and 9B). Additionally, when compared at the same dose level, AUCs measured for the 5 kDa-100% were higher than those observed for the 2-kDa-100% conjugates. A difference of 21%, 37% and 514% were consistently found in favor of the 5 kDa-100% conjugate, at the 5, 25 and 50 U/kg doses, respectively (FIG. 8). The 5 kDa-100% conjugate also appeared to have a longer half-life than Oncaspar itself when tested at the same dose on a protein content basis, as shown in FIGS. 9A and 9B and in the derived pharmacokinetic parameters shown in Table 4. The superior pharmacokinetic profiles for the *Erwinia* conjugates are surprising, since *E. coli*-derived L-asparaginase is known to have a longer half-life in human and in animals than *Erwinia chrysanthemi*-derived L-asparaginase (crisantaspase). Hence, a longer half-life would have logically been predicted for PEGylated *E. coli* L-asparaginase (pegaspargase) compared to PEGylated r-crisantaspase. However, unexpectedly and advantageously, the PEGylated r-crisantaspase has a longer half-life than pegaspargase.

Table 5, below, summarizes pharmacokinetic and pharmacodynamic data gathered from several experiments, including those described in Examples 7-9 herein, showing that: 1) both the 2 kDa-100% and the 5 kDa-100% conjugates were highly potent in increasing potency and duration of action of crisantaspase, as shown by the marked differences observed compared to Erwinase®; 2) the 5 kDa-100% conjugate was longer-acting than both the 2 kDa-100% conjugate and Oncaspar®, as shown by a longer half-life observed at all doses tested. In view of the surprisingly inferior results obtained with the 10 kDa-100% conjugate, these data suggest that the benefit of PEGylation increases with the size of the PEG moiety anchored to the crisantaspase up to 5 kDa. The higher molecular weight PEG did not add further benefit, and, at least in the case of 10 kDa, might be even be detrimental. This is unexpected and contrary to results that were seen e.g., when Holtsberg et. al conjugated varying molecular weights of PEG to arginine deaminase, another amino acid degrading enzyme isolated from a microbial source. In those studies pharmacokinctic and pharmacodynamic function of the argininc deaminase enzyme increased as the size of the PEG attachment increased from a molecular weight of 5000 Da to 20,000 Da (Holtsberg, F. W., *Journal of Controlled Release* 80 (2002), 259-271), incorporated herein by reference in its entirety).

TABLE 5

| | Erwinase ® | 2 kDA-100% mPEG-r-crisantaspase | | 5 kDA-100% mPEG-r-crisantaspase | | Oncaspar ® | |
|---|---|---|---|---|---|---|---|
| Dose (µg/kg) | 520 | 10 | 50 | 10 | 50 | 10 | 50 |
| Dose (U/kg) | 250 | 5 | 25 | 5 | 25 | 1 | 5 |
| T½ (h) | 6 | 31 | 55 | 38 | 63 | 28 | 51 |
| Duration of L-asparagine depletion (days) | 2 | 2-3 | 6 | 3-4 | 10+ | 3 | 8+ |

In addition, as seen in more detail below, the immunogenicity data showed that the 10 kDa-100% exhibited an unacceptable immunogenicity profile, a major drawback when considering administering the compound to patients who are allergic to *E. coli* L-asparaginase or have developed anti-L-asparaginase antibodies. In this respect, the 10 kDa-100% conjugate is really not suitable. The 2 kDa-100% and the 5 kDa-100% are preferable, and the 5 kDa-100% conjugate is particularly preferable.

Example 10

Immunogenicity

Immunogenicity of mPEG-r-crisantaspase conjugates was determined in B6D2F1-Hybrids (immune competent, females), Charles River Germany Animals were treated twice a week in weeks 1, 2, 3, 4, an 8 by i.v. injection of 250 U/kg bw for Erwinase® and 5 U/kg bw for all r-crisantaspase conjugates. Serum samples were collected at −1 h pre-dose and after 1 w, 2 w, 4 w, 6 w and 8 w from the orbital sinus. Anti-crisantaspase or anti-mPEG-r-crisantaspase antibody levels in serum were determined by ELISA. The results are summarized in FIGS. 10, 11A and 11B.

High titers of anti-crisantaspase antibodies were observed for Erwinase® starting at week 2 and were maintained for the whole study period. In contrast, no significant antibody levels were observed for r-crisantaspase conjugates (FIG. 10).

As shown in FIGS. 11A and 11B, the production of anti-conjugate antibodies remained of low intensity and frequency for the 2 kDa and 5 kDa mPEG-r-crisantaspase conjugates, and increased with higher values and frequency for the 10 kDa mPEG-r-crisantaspase conjugates. No clear difference was noted between the fully and partially PEGylated conjugates (not shown).

Thus, these data demonstrated that the PEGylation strategy that was selected reduced the immunogenicity of the conjugates compared to the unmodified L-asparaginase, markedly decreasing the anti-crisantaspase antibody response. However, anti-conjugate antibodies were detected, especially with the 10 kDa conjugates, and with a lower intensity with the 2 kDa and 5 kDa conjugates.

In conclusion, it appears that, up to 5 kDa, PEGylation succeeded in improving pharmacokinetic profile, potency and duration of action of r-crisantaspase, while reducing immunogenicity when compared to the unmodified protein, with a potency and duration of action increasing with the size of the polymer used, the 5 kDa mPEG-r-crisantaspase conjugate being slightly more potent that the 2 kDa mPEG-r-crisantaspase conjugate. However, further increasing the size of the PEG to 10 kDa failed to further improve potency and duration of action, as the 10 kDa mPEG-r-crisantaspase conjugate was less potent in vivo than the 5 kDa mPEG-r-crisantaspase conjugate, despite similar in vitro potencies. In addition, the 10 kDa mPEG-r-crisantaspase conjugates exhibited an unacceptable immunogenicity profile, an unexpected result in view of published results with other proteins.

While embodiments and applications of the present invention have been described in some detail by way of illustration and example, it would be apparent to those of skill in the art 15 that many additional modifications would be possible without departing from the inventive concepts contained herein. All references cited herein are hereby incorporated in their entirety.

What is claimed is:

1. A conjugate comprising an L-asparaginase from *Erwinia chrysanthemi* having at least 90% sequence identity to the amino acid of SEQ ID NO:1 and conjugated to at least one polyethylene glycol (PEG) molecule, wherein the at least one PEG has a molecular weight less than 5000, 4000, 3000, or 2500 Da and the conjugate has at least fifty times more in vivo L-asparaginase activity compared to an *Erwinia chrysanthemi* L-asparaginase not conjugated to PEG.

2. The conjugate of claim 1, wherein said L-asparaginase has at least 95% to 99% sequence identity to the amino acid of SEQ ID NO: 1.

3. The conjugate of claim 1, wherein said L-asparaginase comprises the amino acid of SEQ ID NO: 1.

4. The conjugate of claim 1, wherein the PEG is covalently linked to one or more amino groups of said L-asparaginase.

5. The conjugate of claim 4, wherein the PEG molecules are covalently linked to at least from about 40% to about 100% of the accessible amino groups of said L-asparaginase.

6. The conjugate of claim 1 having the formula:

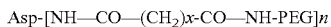

Asp-[NH—CO—(CH$_2$)$x$-CO—NH-PEG]$n$ wherein Asp is the L-asparaginase, NH is one or more of the NH groups of the lysine residues and/or the N-terminus in the Asp, PEG is a polyethylene glycol moiety, n is a number that represents at least 40% to 100% of the accessible amino groups in the Asp, and x is an integer ranging from 1 to 8.

7. The conjugate of claim 1, wherein said PEG is monomethoxy-polyethylene glycol.

8. The conjugate of claim 1, wherein said conjugate has at least sixty, seventy, eighty, ninety or one-hundred times more in vivo L-asparaginase activity compared to an *Erwinia chrysanthemi* L-asparaginase not conjugated to PEG.

9. The conjugate of claim 1, wherein the conjugate has increased residual enzymatic activity in vivo when compared to *Erwinia chrysanthemi* L-asparaginase conjugated to at least one PEG molecule with a molecular weight of 10,000 Da.

10. The conjugate of claim 1, wherein the L-asparaginase does not cross-react with antibodies which react with *Escherichia coli* L-asparaginase.

11. The conjugate of claim 1 comprising an L-asparaginase from *Erwinia chrysanthemi* consisting of the amino acid of SEQ ID NO: 1 and the conjugate has reduced immunogenicity when administered to a human subject hypersensitive to *Escherichia coli* L-asparaginase.

12. The conjugate of claim 1, wherein the conjugate has an in vitro L-asparaginase activity of at least 60%, 70%, 80%, or 87% of an L-asparaginase not conjugated to PEG.

13. The conjugate of claim 1, wherein said PEG has a molecular weight of less than 5000 Da.

14. The conjugate of claim 1, wherein the PEG molecules are covalently linked to at least 60%, 70%, 80%, 90% or 100% of the accessible amino groups of said L-asparaginase.

* * * * *

SEQUENCE LISTING

```
<160> NUMBER OF SEQ ID NOS: 1

<210> SEQ ID NO 1
<211> LENGTH: 327
<212> TYPE: PRT
<213> ORGANISM: Erwinia chrysanthemi

<400> SEQUENCE: 1

Ala Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Glu Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
```

|  | 195 |  |  |  | 200 |  |  |  | 205 |  |  |
|---|---|---|---|---|---|---|---|---|---|---|---|
| Phe | Asp 210 | Val | Arg | Gly | Leu | Thr 215 | Ser | Leu | Pro | Lys | Val Asp 220 Ile Leu Tyr |

| Gly 225 | Tyr | Gln | Asp | Asp | Pro 230 | Glu | Tyr | Leu | Tyr | Asp 235 | Ala | Ala | Ile | Gln | His 240 |

| Gly | Val | Lys | Gly | Ile 245 | Val | Tyr | Ala | Gly | Met 250 | Gly | Ala | Gly | Ser | Val 255 | Ser |

| Val | Arg | Gly | Ile 260 | Ala | Gly | Met | Arg | Lys 265 | Ala | Met | Glu | Lys | Gly 270 | Val | Val |

| Val | Ile | Arg 275 | Ser | Thr | Arg | Thr | Gly 280 | Asn | Gly | Ile | Val | Pro 285 | Pro | Asp | Glu |

| Glu | Leu | Pro 290 | Gly | Leu | Val | Ser 295 | Asp | Ser | Leu | Asn | Pro 300 | Ala | His | Ala | Arg |

| Ile 305 | Leu | Leu | Met | Leu 310 | Ala | Leu | Thr | Arg | Thr 315 | Ser | Asp | Pro | Lys | Val | Ile 320 |

| Gln | Glu | Tyr | Phe | His 325 | Thr | Tyr |